United States Patent
Gerber et al.

(10) Patent No.: US 7,801,619 B2
(45) Date of Patent: *Sep. 21, 2010

(54) TREE-BASED ELECTRICAL STIMULATOR PROGRAMMING FOR PAIN THERAPY

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 171 days.

This patent is subject to a terminal disclaimer.

(21) Appl. No.: 11/799,114

(22) Filed: Apr. 30, 2007

(65) Prior Publication Data

US 2007/0265681 A1 Nov. 15, 2007

Related U.S. Application Data

(63) Continuation-in-part of application No. 11/414,527, filed on Apr. 28, 2006.

(51) Int. Cl.
*A61N 1/18* (2006.01)
(52) U.S. Cl. .......................................... 607/59; 607/2
(58) Field of Classification Search .................. 607/59
See application file for complete search history.

(56) References Cited

U.S. PATENT DOCUMENTS

| | | | |
|---|---|---|---|
| 4,236,524 A | 12/1980 | Powell et al. |
| 4,872,122 A | 10/1989 | Altschuler et al. |
| 4,895,574 A | 1/1990 | Rosenberg |
| 5,005,143 A | 4/1991 | Altschuler et al. |
| 5,240,009 A | 8/1993 | Williams |
| 5,280,792 A | 1/1994 | Leong et al. |

(Continued)

FOREIGN PATENT DOCUMENTS

EP 0 541 338 B1 5/1993

(Continued)

OTHER PUBLICATIONS

"Notice of Transmittal of the International Search Report and the Written Opinion of the International Searching Authority, or the Declaration," dated Jan. 16, 2008 for corresponding PCT Application No. PCT/US2007/010381, (12 pgs.).

(Continued)

*Primary Examiner*—Carl H Layno
*Assistant Examiner*—Jeremiah T Kimball
(74) *Attorney, Agent, or Firm*—Shumaker & Sieffert, P.A.

(57) ABSTRACT

The disclosure describes an implantable stimulation system that guides programming with a therapeutic tree. All possible stimulation parameters are arranged on the therapeutic tree, with each level of the therapeutic tree containing a different stimulation parameter type. Each level includes nodes that are connected to nodes of adjacent levels. A program path is created by moving through nodes of lower levels. The stimulation parameter types are arranged so that coarse adjustments occur at higher levels of the tree and fine adjustments occur at lower levels of the tree. The nodes of the program path define the stimulation parameters of the delivered stimulation therapy. The user may provide information such as efficacy input and/or medication dosage information to the system for identifying the most efficacious program path in treating pain of the patient. Additionally or alternatively, efficacy feedback may be received from physiological parameter sensors.

36 Claims, 13 Drawing Sheets

U.S. PATENT DOCUMENTS

| | | | |
|---|---|---|---|
| 5,358,513 A | 10/1994 | Powell, III et al. |
| 5,383,910 A | 1/1995 | den Dulk |
| 5,443,486 A | 8/1995 | Hrdlicka et al. |
| 5,522,863 A | 6/1996 | Spano et al. |
| 5,626,140 A | 5/1997 | Feldman et al. |
| 5,645,069 A | 7/1997 | Lee |
| 5,673,367 A | 9/1997 | Buckley |
| 5,702,429 A | 12/1997 | King |
| 5,706,403 A | 1/1998 | Shibata et al. |
| 5,713,932 A | 2/1998 | Gillberg et al. |
| 5,716,382 A | 2/1998 | Snell |
| 5,774,357 A | 6/1998 | Hoffberg et al. |
| 5,782,885 A | 7/1998 | Andersson |
| 5,810,014 A | 9/1998 | Davis et al. |
| 5,867,386 A | 2/1999 | Hoffberg et al. |
| 5,875,108 A | 2/1999 | Hoffberg et al. |
| 5,901,246 A | 5/1999 | Hoffberg et al. |
| 5,903,454 A | 5/1999 | Hoffberg et al. |
| 5,920,477 A | 7/1999 | Hoffberg et al. |
| 5,921,937 A | 7/1999 | Davis et al. |
| 5,938,688 A | 8/1999 | Schiff |
| 5,995,868 A | 11/1999 | Dorfmeister et al. |
| 5,999,854 A | 12/1999 | Deno et al. |
| 6,038,476 A | 3/2000 | Schwartz |
| 6,081,750 A | 6/2000 | Hoffberg et al. |
| 6,129,745 A | 10/2000 | Sun et al. |
| 6,171,239 B1 | 1/2001 | Humphrey |
| 6,192,273 B1 | 2/2001 | Igel et al. |
| 6,263,230 B1 | 7/2001 | Haynor et al. |
| 6,269,267 B1 | 7/2001 | Bardy et al. |
| 6,308,102 B1 | 10/2001 | Sieracki et al. |
| 6,345,200 B1 | 2/2002 | Mouchawar et al. |
| 6,370,423 B1 | 4/2002 | Guerrero et al. |
| 6,385,479 B1 | 5/2002 | Sibbitt et al. |
| 6,386,882 B1 | 5/2002 | Linberg |
| 6,400,996 B1 | 6/2002 | Hoffberg et al. |
| 6,408,290 B1 | 6/2002 | Thiesson et al. |
| 6,418,424 B1 | 7/2002 | Hoffberg et al. |
| 6,434,261 B1 | 8/2002 | Zhang et al. |
| 6,456,622 B1 | 9/2002 | Skaanning et al. |
| 6,473,653 B1 | 10/2002 | Schallhorn et al. |
| 6,480,743 B1 | 11/2002 | Kirkpatrick et al. |
| 6,480,814 B1 | 11/2002 | Levitan |
| 6,496,816 B1 | 12/2002 | Thiesson et al. |
| 6,497,655 B1 | 12/2002 | Linberg et al. |
| 6,522,928 B2 | 2/2003 | Whitehurst et al. |
| 6,530,954 B1 | 3/2003 | Eckmiller |
| 6,539,249 B1 | 3/2003 | Kadhiresan et al. |
| 6,539,263 B1 | 3/2003 | Schiff et al. |
| 6,547,746 B1 | 4/2003 | Marino |
| 6,549,804 B1 | 4/2003 | Osorio et al. |
| 6,554,762 B2 | 4/2003 | Leysieffer |
| 6,556,699 B2 | 4/2003 | Rogers et al. |
| 6,572,542 B1 | 6/2003 | Houben et al. |
| 6,575,894 B2 | 6/2003 | Leysieffer et al. |
| 6,597,943 B2 | 7/2003 | Taha et al. |
| 6,609,017 B1 | 8/2003 | Shenoy et al. |
| 6,609,032 B1 * | 8/2003 | Woods et al. ............ 607/46 |
| 6,612,983 B1 | 9/2003 | Marchal |
| 6,658,287 B1 | 12/2003 | Litt et al. |
| 6,659,968 B1 | 12/2003 | McClure |
| 6,662,051 B1 | 12/2003 | Eraker et al. |
| 6,687,538 B1 | 2/2004 | Hrdlicka et al. |
| 6,697,672 B2 | 2/2004 | Andersson |
| 6,704,595 B2 | 3/2004 | Bardy |
| 7,050,856 B2 | 5/2006 | Stypulkowski |
| 7,123,961 B1 * | 10/2006 | Kroll et al. ............ 607/9 |
| 7,142,923 B2 | 11/2006 | North et al. |
| 7,415,308 B2 * | 8/2008 | Gerber et al. ............ 607/41 |
| 2002/0016699 A1 | 2/2002 | Hoggart et al. |
| 2002/0038294 A1 | 3/2002 | Matsugu |
| 2002/0045804 A1 | 4/2002 | Christopherson et al. |
| 2002/0055779 A1 | 5/2002 | Andrews |
| 2002/0087201 A1 | 7/2002 | Firlik et al. |
| 2002/0091419 A1 | 7/2002 | Firlik et al. |
| 2002/0103512 A1 | 8/2002 | Echauz et al. |
| 2002/0123673 A1 | 9/2002 | Webb et al. |
| 2002/0138013 A1 | 9/2002 | Guerrero et al. |
| 2002/0151992 A1 | 10/2002 | Hoffberg et al. |
| 2003/0041866 A1 | 3/2003 | Linberg et al. |
| 2003/0043815 A1 | 3/2003 | Tinsley et al. |
| 2003/0050568 A1 | 3/2003 | Green et al. |
| 2003/0053663 A1 | 3/2003 | Chen et al. |
| 2003/0088274 A1 | 5/2003 | Gliner et al. |
| 2003/0093129 A1 | 5/2003 | Nicolelis et al. |
| 2003/0097159 A1 | 5/2003 | Schiff et al. |
| 2003/0097161 A1 | 5/2003 | Firlik et al. |
| 2003/0105409 A1 | 6/2003 | Donoghue et al. |
| 2003/0135248 A1 | 7/2003 | Stypulkowski |
| 2003/0158587 A1 | 8/2003 | Esteller et al. |
| 2003/0195569 A1 | 10/2003 | Swerdlow et al. |
| 2003/0216620 A1 | 11/2003 | Jain et al. |
| 2003/0216654 A1 | 11/2003 | Xu et al. |
| 2004/0103001 A1 | 5/2004 | Mazar et al. |
| 2004/0129271 A1 | 7/2004 | Hickle |
| 2004/0143302 A1 | 7/2004 | Sieracki et al. |
| 2004/0199217 A1 | 10/2004 | Lee et al. |
| 2004/0215288 A1 | 10/2004 | Lee et al. |
| 2004/0267330 A1 | 12/2004 | Lee et al. |
| 2005/0043774 A1 | 2/2005 | Devlin et al. |
| 2005/0060007 A1 * | 3/2005 | Goetz ............ 607/48 |
| 2005/0060008 A1 | 3/2005 | Goetz |
| 2005/0060009 A1 | 3/2005 | Goetz |
| 2005/0060010 A1 | 3/2005 | Goetz |
| 2005/0075669 A1 * | 4/2005 | King ............ 607/2 |
| 2005/0080462 A1 | 4/2005 | Jenkins et al. |
| 2005/0177206 A1 | 8/2005 | North et al. |
| 2005/0209644 A1 * | 9/2005 | Heruth et al. ............ 607/3 |
| 2005/0222643 A1 | 10/2005 | Heruth et al. |
| 2005/0245988 A1 | 11/2005 | Miesel |
| 2006/0020292 A1 | 1/2006 | Goetz et al. |
| 2006/0190047 A1 | 8/2006 | Gerber et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0190061 A1 | 8/2006 | Stypulkowski |
| 2006/0195145 A1 | 8/2006 | Lee et al. |
| 2006/0206162 A1 | 9/2006 | Wahlstrand et al. |
| 2006/0206163 A1 | 9/2006 | Wahlstrand et al. |
| 2006/0235472 A1 | 10/2006 | Goetz et al. |
| 2006/0259099 A1 * | 11/2006 | Goetz et al. ............ 607/66 |
| 2006/0270944 A1 | 11/2006 | King |

FOREIGN PATENT DOCUMENTS

| | | |
|---|---|---|
| EP | 0 653 224 A2 | 5/1995 |
| EP | 0 653 224 B1 | 5/1995 |
| EP | 0 684 858 B1 | 12/1995 |
| EP | 0 756 877 A2 | 2/1997 |
| EP | 0 796 636 A1 | 9/1997 |
| EP | 0 848 965 A2 | 6/1998 |
| EP | 0 848 965 B1 | 6/1998 |
| EP | 0 882 469 B1 | 12/1998 |
| EP | 1 192 971 B1 | 4/2002 |
| WO | WO 00/10455 A1 | 3/2000 |
| WO | WO 01/17419 A1 | 3/2001 |
| WO | WO 01/43823 A1 | 6/2001 |
| WO | WO 01/47600 A1 | 7/2001 |
| WO | WO 01/56467 A1 | 8/2001 |
| WO | WO 01/60445 A2 | 8/2001 |
| WO | WO 01/82995 A3 | 11/2001 |
| WO | WO 02/02622 A2 | 1/2002 |
| WO | WO 02/15777 A1 | 2/2002 |
| WO | WO 03/043690 A1 | 5/2003 |

| | | |
|---|---|---|
| WO | WO 03/051175 A2 | 6/2003 |
| WO | WO 03/094721 A1 | 11/2003 |
| WO | WO 2004/041352 A1 | 5/2004 |
| WO | WO 2004/075982 A1 | 9/2004 |
| WO | WO 2004/096349 A1 | 11/2004 |
| WO | WO 2004/096358 A2 | 11/2004 |
| WO | WO 2005/028028 A1 | 3/2005 |
| WO | WO 2005/039688 A2 | 5/2005 |
| WO | WO 2005/089648 A1 | 9/2005 |
| WO | WO 2006/012423 A1 | 2/2006 |
| WO | WO 2006/098823 A1 | 9/2006 |
| WO | WO 2006/098824 A1 | 9/2006 |

OTHER PUBLICATIONS

"Reply to Written Opinion," dated Mar. 20, 2008 for corresponding PCT Application No. PCT/US2007/010381, (8 pgs.).

Notification of Transmittal of the International Preliminary Report on Patentability dated Aug. 19, 2008 for corresponding PCT Application Serial No. PCT/US2007/010381 (10 pgs).

Office Action dated Dec. 31, 2008 for U.S. Appl. No. 11/414,527 (12 pgs.).

Responsive Amendment dated Mar. 31, 2009 for U.S. Appl. No. 11/414,527 (18 pgs.).

Office Action dated Jan. 12, 2009 for U.S. Appl. No. 11/799,113 (15 pgs.).

Responsive Amendment dated Apr. 13, 2009 for U.S. Appl. No. 11/799,113 (20 pgs.).

European Office Action dated May 29, 2009 for Application No. 07 794 413.0-1265 (2 pgs.).

Office Action dated Sep. 2, 2009 for U.S. Appl. No. 11/414,527 (12 pgs.).

Office Action dated Sep. 4, 2009 for U.S. Appl. No. 11/799,113 (14 pgs.).

Response dated Nov. 2, 2009 for U.S. Appl. No. 11/414,527 (7 pgs.).

Response dated Nov. 4, 2009 for U.S. Appl. No. 11/799,113 (11 pgs.).

U.S. Appl. No. 11/799,113, filed Apr. 30, 2007, entitled "Tree-Based Electrical Stimulator Programming," by Gerber et al.

U.S. Appl. No. 11/414,527, filed Apr. 28, 2006, entitled "Tree-Based Electrical Stimulator Programming", by Rondoni et al.

\* cited by examiner

TREE-BASED ELECTRICAL STIMULATOR PROGRAMMING FOR PAIN THERAPY

This application is a continuation-in-part of U.S. application Ser. No. 11/414,527, filed Apr. 28, 2006, the entire content of which is incorporated herein by reference.

TECHNICAL FIELD

The invention relates to medical devices and, more particularly, electrical stimulators.

BACKGROUND

Electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target locations associated with the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

In general, a clinician selects values for a number of programmable parameters in order to define the electrical stimulation therapy to be delivered by the implantable stimulator to a patient. For example, the clinician ordinarily selects a combination of electrodes carried by one or more implantable leads, and assigns polarities to the selected electrodes. In addition, the clinician selects an amplitude, which may be a current or voltage amplitude, a pulse width, and a pulse rate for stimulation pulses to be delivered to the patient. A group of parameters, including electrode configuration (electrode combination and electrode polarity), amplitude, pulse width and pulse rate, may be referred to as a program in the sense that they drive the neurostimulation therapy to be delivered to the patient.

The process of selecting stimulation parameters can be time consuming, and may require a great deal of trial and error before a therapeutic program is discovered. The "best" program may be a program that best balances greater clinical efficacy and minimal side effects experienced by the patient. In addition, some programs may consume less power during therapy. The clinician may test stimulation parameters by manually specifying parameters based on intuition or some idiosyncratic methodology. The clinician may then record notes on the efficacy and side effects of each parameter set after delivery of stimulation via that combination. Upon receipt of patient feedback and/or observation of symptoms by the clinician, the clinician is able to compare and select from the tested programs.

SUMMARY

The disclosure is directed to techniques for guiding the programming of an electrical stimulator using a therapeutic tree and efficacy feedback from a user. Each level of the tree includes nodes that are connected to nodes of adjacent levels, similar to a branching tree. A user, such as a clinician or a patient, creates a program path by moving through one node at each level of the tree according to efficacy feedback. In this manner, the therapeutic tree may create an effective stimulation therapy program to treat pain of the patient.

Electrical stimulation therapy is generally defined by a group of parameters, including electrode combination, electrode polarity, current or voltage amplitude, stimulation pulse width, and stimulation pulse rate. A variety of stimulation parameters are associated with the nodes in the therapeutic tree. In particular, each level of the therapeutic tree contains nodes representing adjustment of a different type of stimulation parameter.

The stimulation parameter types may be arranged so that higher priority adjustments occur at higher levels of the tree and lower priority adjustments occur at lower levels of the tree. In particular, the parameters are prioritized so that parameters believed to have the largest impact on efficacy are placed in upper levels of the tree, while parameters having lesser impacts are placed in lower levels of the tree. For example, one level of the tree may contain nodes that represent adjustments to pulse rate, while another level of the tree contains nodes that represent adjustments to pulse width, and yet another level contains nodes that represent adjustments in pulse amplitude.

The nodes of the program path define the stimulation parameters of the delivered stimulation therapy. A clinician or patient traverses the levels and nodes of the tree based on efficacy feedback from the patient, objective efficacy observations by the clinician, and/or sensed physiological conditions indicative of efficacy. The efficacy feedback permits navigation of an efficacious program path, resulting in a set of stimulation parameter values that support therapeutic efficacy.

If a selected node of the tree produces a therapeutic efficacy improvement that exceeds a threshold level, then programming proceeds down the tree to the next level of nodes connected to the selected node. If the selected node does not produce an efficacy improvement above the threshold level, then programming proceeds to other nodes at the same level of the tree as the selected node. The threshold level may be a subjective pain level based upon normal pain perceived by the patient without therapy.

For example, if a selected node corresponding to a particular pulse rate change is evaluated and found to yield a sufficient efficacy improvement with regard to pain reduction, the process proceeds to nodes at the next level of the tree, which may represent adjustments to a pulse width value. While adjustments to pulse width are evaluated, the pulse rate value specified by the node in the upper level is maintained. Eventually, when a suitable pulse width value improvement is found, the process may proceed to nodes in the next level of the tree to evaluate amplitude adjustments. In this case, the pulse rate and pulse width are held constant according to the selected nodes in the upper levels of the tree while different amplitudes are evaluated.

A therapeutic tree, in accordance with this disclosure, may guide a clinician, a patient, a stimulator, or a programming device to programs containing effective parameters. A stimulator, for example, may communicate with an external programmer that receives patient or clinician input. The stimulator may also communicate with one or more sensors that measure a physiological parameter of the patient via a wired or wireless connection. The sensor may provide objective feedback or efficacy input. When efficacy input from the patient, clinician, or sensor indicates the improved or worsened pain therapy, the external programmer or stimulator may automatically traverse the therapeutic tree to modify the program for improved efficacy. In addition, the patient may input the dosage and frequency of pain medication taken to indicate how well the stimulation therapy is treating the patient's pain. Hence, the therapeutic tree may be used in initial programming of the stimulator by a clinician or patient, and/or during normal operation by the stimulator.

In one embodiment, the disclosure provides a method for providing electrical stimulation pain therapy, the method comprising defining a tree structure having a plurality of levels and a plurality of nodes in each of the levels, wherein each of the nodes is interconnected with at least one node above and at least two nodes below in the tree structure, each node defines a set of electrical stimulation parameters, the nodes in each level specify an adjustment to at least one of the parameters, and the nodes in different levels specify the adjustment of different parameters, defining a program path through the tree structure along a series of the interconnected nodes for which efficacy of stimulation pain therapy delivered according to the stimulation parameters defined by the nodes exceeds a threshold level, selecting one of the nodes in the program path, and delivering the stimulation pain therapy to a patient based on the parameters defined by the selected node to treat patient pain.

In another embodiment, the disclosure provides a system for providing electrical stimulation pain therapy, the system comprising a memory defining a tree structure having a plurality of levels and a plurality of nodes in each of the levels, wherein each of the nodes is interconnected with at least one node above and at least two nodes below in the tree structure, each node defines a set of electrical stimulation parameters, the nodes in each level specify an adjustment to at least one of the parameters, and the nodes in different levels specify the adjustment of different parameters, and a processor that defines a program path through the tree structure along a series of the interconnected nodes for which efficacy of stimulation pain therapy delivered according to the stimulation parameters defined by the nodes exceeds a threshold level, selects one of the nodes in the program path, and controls delivery of the stimulation pain therapy to a patient based on the parameters defined by the selected node to treat patient pain.

In an additional embodiment, the disclosure provides a computer-readable medium comprising instructions to cause a processor to define a tree structure having a plurality of levels and a plurality of nodes in each of the levels, wherein each of the nodes is interconnected with at least one node above and at least two nodes below in the tree structure, each node defines a set of electrical stimulation parameters, the nodes in each level specify an adjustment to at least one of the parameters, and the nodes in different levels specify the adjustment of different parameters, define a program path through the tree structure along a series of the interconnected nodes for which efficacy of stimulation pain therapy delivered according to the stimulation parameters defined by the nodes exceeds a threshold level, select one of the nodes in the program path, and control delivery of the stimulation pain therapy to a patient based on the parameters defined by the selected node to treat patient pain.

In various embodiments, the invention may provide one or more advantages. For example, the therapeutic tree provides a method to guide a user to find more efficacious stimulation therapy for alleviating pain based upon patient feedback or sensor feedback. The patient feedback may include pain experienced by the patient and/or medication doses taken by the patient which indicate the efficacy of the current therapy. In addition, the therapeutic tree may be weighted by the clinician to change how the program path is created. The patient may benefit by achieving better stimulation therapy than would be found using trial and error or other stimulation parameter search mechanisms, or by achieving acceptable stimulation therapy more quickly.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
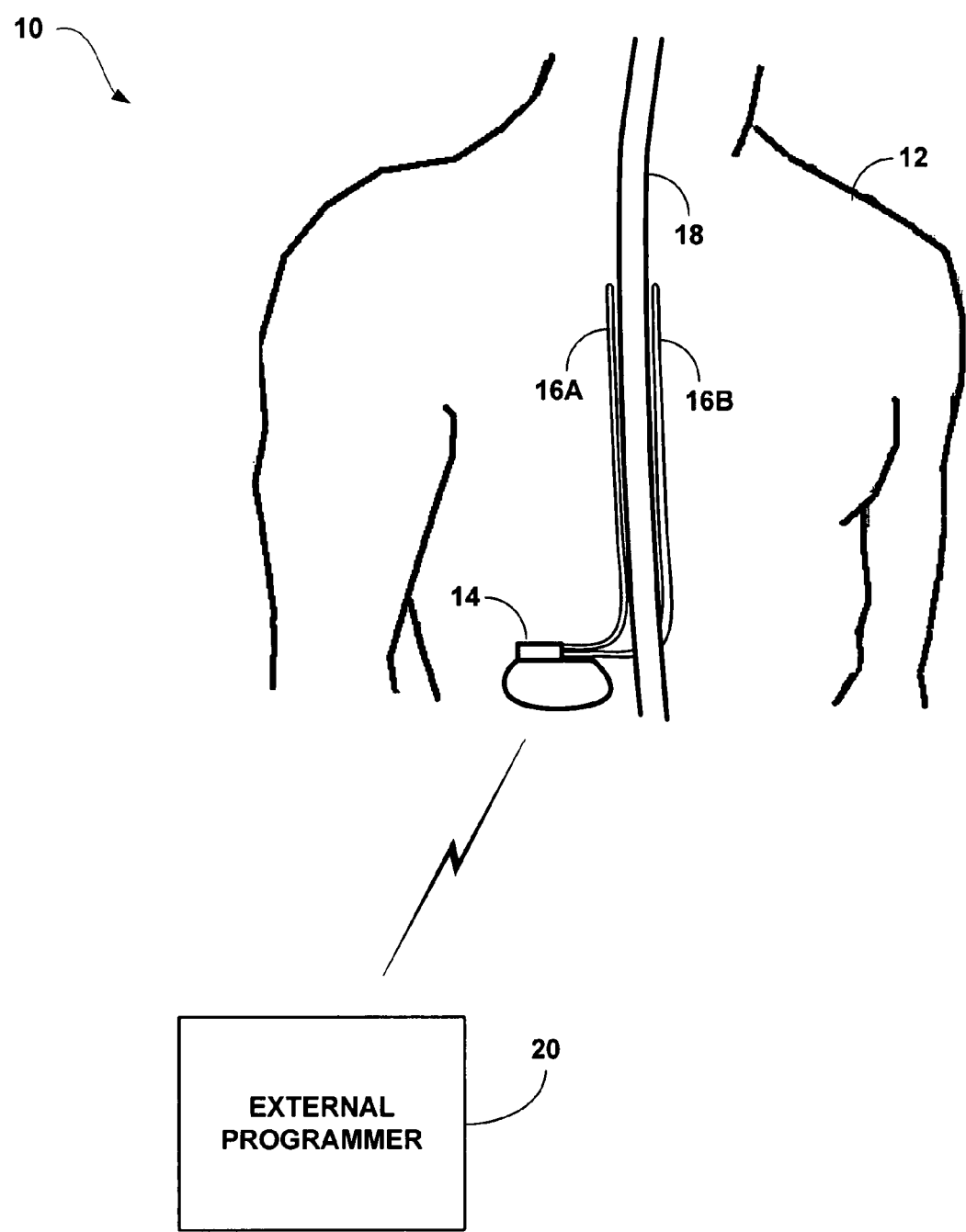
FIG. 1 is a schematic diagram illustrating an implantable spinal cord stimulation system in which stimulation is programmed based upon a therapeutic tree.

The disclosure is directed to techniques for guiding the programming of an electrical stimulator using a therapeutic tree and efficacy feedback. The techniques may be applicable to a variety of different electrical stimulators, including implantable electrical stimulators configured to deliver electrical stimulation therapy to patients to treat a variety of symptoms or conditions such as chronic pain, temporary pain, or any other pain perceived by the patient.

The stimulator may deliver neurostimulation therapy via one or more leads that include electrodes located proximate to target locations associated with the spinal cord, peripheral nerves, or any other nerves associated with pain perception. Stimulation may be used in different therapeutic applications, such as spinal cord stimulation (SCS), deep brain stimulation (DBS), cortical stimulation (CS), peripheral nerve stimulation (PNS), and peripheral nerve field stimulation (PNFS). In general, PNFS may be similar to PNS. However, for PNFS, the stimulation is generally not directed to any particular peripheral nerve, and is instead delivered generally to the area in which the patient experiences pain.

In this disclosure, for purposes of illustration, the techniques for guiding programming will be described in the context of electrical stimulation therapy for pain management therapy. Both SCS and PNFS are described in the context of guiding programming using a therapeutic tree, but SCS will be used as the primary example throughout this disclosure.

Chronic pain may be a debilitating condition for a patient. Pain may prevent the patient from performing certain activities, interacting with other people in social situations, or even sleeping regularly. Chronic pain may be the result of injury, disease, age, or other conditions. Pain may originate at organs, muscles, nerves, or other tissues, and most pain signals are transferred though the spinal cord. Electrical stimulation of certain nerves, nerve plexuses, or the spinal cord may provide an effective therapy for pain experienced by the patient. Stimulation of the brain may also be effective for alleviating pain, such as neuropathic or nociceptive pain.

In some embodiments of the invention, an implantable electrical stimulator may be provided. In some cases, electrical stimulation may permanently reduce chronic pain. However, in other cases, stimulation with the same stimulation parameter set may become less efficacious through time due to accommodation. The electrical stimulator may be a stimulator that delivers electrical stimulation to, for example, a portion of the spinal cord to block pain signals being transferred to the brain of the patient.

An electrical stimulator may be capable of thousands of different stimulation parameter sets, or programs that define the stimulation therapy. Providing a method to program the stimulation therapy to achieve the most efficacious therapy is important to patient health and quality of life. Without an effective tool to guide a user through selecting each stimulation parameter, the patient may not benefit from an optimal therapy program. In addition, the patient may not be able to effectively modify the stimulation program during chronic therapy.

A therapeutic tree, in accordance with this disclosure, guides a user, such as a patient or physician, to create a program path when setting initial chronic stimulation parameters or modifying current stimulation programs. Stimulation parameter types, such as electrode configuration, pulse rate, pulse width, and voltage amplitude, are arranged in the therapeutic tree so that the program path that connects multiple nodes of the tree defines the stimulation.

Feedback from the patient or clinician, or a sensor, may be used to create a program path that provides efficacious therapy for the patient. For example, if the therapeutic efficacy of stimulation delivered according to parameters associated with a selected node in the tree is increased by more than a threshold level, e.g., 50%, relative to the patient's baseline condition, the therapeutic tree will guide the user downward to nodes at the next level connected to the effective node. In this manner, the set of parameters can be refined to pursue further improvements.

Alternatively, if the efficacy improvement does not exceed the threshold, the therapeutic tree may guide the user up the tree to evaluate different nodes at the same level as the selected node. The structure of the therapeutic tree and efficacy feedback combine to decrease programming time and improve stimulation therapy efficacy, which may effectively improve patient quality of life.

In this disclosure, a therapeutic tree structure and a variety of efficacy feedback media, including patient input, clinician input, pain medication taken, and sensor-based feedback are described for purposes of illustration. The feedback may include multiple inputs that the system uses in determining the efficacy of the stimulation pain therapy. For example, increased medication taken by the patient may indicate that stimulation therapy is not effective at controlling the patient's pain. However, the particular feedback implementations are merely for purposes of example, and should not be considered limiting of the invention as broadly embodied and described in this disclosure.

FIG. 1 is a schematic diagram illustrating an implantable spinal cord stimulation (SCS) system in which stimulation is programmed based upon a therapeutic tree. As shown in FIG. 1, system 10 includes implantable stimulator 14 and external programmer 20 shown in conjunction with a patient 12. Stimulation pulses are delivered to spinal cord 18 of patient 12 via one or more electrodes of leads 16A and 16B (collectively "leads 16"), where the electrode is placed adjacent to the target tissue of the spinal cord. In the example of FIG. 1, stimulation pulses are delivered to the spinal cord 18 to reduce the amount of pain perceived by patient 12. As mentioned above, however, the stimulator may be used with a variety of different pain therapies, such as peripheral nerve stimulation (PNS), peripheral nerve field stimulation (PNFS), deep brain stimulation (DBS), cortical stimulation (CS), and the like.

With reference to FIG. 1, a user, such as a clinician or patient 12, may interact with a user interface of external programmer 20 to provide system 10 with feedback indicating the efficacy of the stimulation pulses. Based on the efficacy feedback from the user, the therapeutic tree (not shown) is used to guide programming of the stimulation therapy. In particular, the efficacy feedback directs programming through selected branches of the tree to identify a program providing desirable efficacy. The term "program" generally refers to a set of stimulation parameters, such as electrode combination, electrode polarity, voltage or current amplitude, pulse width and/or pulse rate.

Stimulator 14 is implanted in patient 12 at a location minimally noticeable to the patient. For SCS, stimulator 14 may be located in the lower abdomen, lower back, or other location. Leads 16 are tunneled from stimulator 14 through tissue to reach the target tissue adjacent to spinal cord 18 for stimulation delivery. At the distal tips of leads 16 are one or more electrodes (not shown) that transfer the stimulation pulses from the lead to the tissue. The electrodes may be pad electrodes located on, for example, a paddle shaped portion of a lead 16, circular (i.e., ring) electrodes surrounding the body of leads 16, conformable electrodes, cuff electrodes, or any other type of electrodes capable of forming unipolar, bipolar or multipolar electrode configurations.

The target tissue may be any tissue affected by electrical pulses. Such tissue includes nerves, smooth muscle, and skeletal muscle. In the example illustrated by FIG. 1, the target tissue is spinal cord 18. Stimulation of spinal cord 18 may, for example, prevent pain signals from traveling through the spinal cord and to the brain of the patient. Patient 12 perceives the interruption of pain signals as a reduction in pain and efficacious therapy.

Before stimulation begins, a clinician, e.g., physician, or patient 12 may evaluate the initial condition of the patient or extent of chronic pain according to specific criteria associated with system 10. This baseline evaluation allows the clinician to compare the efficacy of the stimulation therapy and modify the therapy as needed. After system 10 is implanted in patient 12 and ready to deliver electrical stimulation therapy, the clinician programs stimulator 14 via external programmer 20. The clinician first selects an initial program that includes pre-selected stimulation parameters according to the type of stimulation needed to treat the pain of patient 12. In some embodiments, the clinician may manually select the initial stimulation parameters based upon previous experience or the baseline evaluation by patient 12.

Patient 12 may evaluate the initial stimulation parameters before further adjustments are made. In this case, the evaluation determines how the therapeutic tree is used to guide the clinician in creating a program path for chronic stimulation pain therapy. If patient 12 determines that initial stimulation parameters provide an efficacy improvement greater than a threshold, such as 50 percent, relative to the patient's baseline condition, the clinician begins to fine tune the program path by evaluating nodes in lower levels of the therapeutic tree. If the therapy efficacy improvement is less than the threshold relative to the baseline, the clinician coarse tunes the program path by utilizing upper levels of the therapeutic tree. In other embodiments, the clinician may bypass the initial evaluation process and directly proceed to program system 10 with the therapeutic tree.

The therapeutic tree is a programming mechanism that aids the clinician and patient 12 in finding effective stimulation parameters for treating the patient. The therapeutic tree includes nodes that are associated with a stimulation parameter type and a stimulation parameter type value. The nodes are arranged in different levels of the therapeutic tree. Each node is connected to one node of a higher level and at one or more nodes of a lower level. The program path begins with a first node of a first level. If the first node is selected, the program path continues to a first node of a second level. The first node of the first level may be connected to two or more nodes of the second level. Each level contains two or more nodes. Fine tuning is used to describe moving to lower levels, e.g., the second level, the third level, and so forth. The stimulation therapy is further defined as the program path increases in the number of nodes connected by the program path. A program path can only contain one node from each level of the therapeutic tree, but the program path may be reversed to create a different program path if the stimulation therapy defined by the first program path fails to effectively treat patient 12.

Each level of the therapeutic tree contains nodes that represent one stimulation parameter type. A stimulation parameter type may include electrode configuration (combination and polarity), pulse rate, pulse width, voltage amplitude, current amplitude, stimulation duration, or any other parameter that would define electrical stimulation therapy. Therefore, the multiple nodes of each level define different values for a particular stimulation parameter type value. For example, the first level may contain electrode configuration nodes, where a first node defines one electrode configuration and a second node defines a different electrode configuration. If leads 16 contain a plurality of electrodes, the first level of the therapeutic tree may contain many nodes. As described herein, the first level is named as such because it is the first level, beyond a root level defining the patient's baseline condition that the clinician would start with when creating a program path.

In some embodiments, which stimulation parameter types are placed in what levels of the therapeutic tree may be pre-configured during or shortly after manufacture of the device that utilizes or provides the tree, or configured by a field technician before system 10 is used by the clinician or patient 12. Alternatively, the clinician or patient may selectively associate parameter types at particular levels of the tree. This association of parameter types with different levels may be viewed as a prioritization of parameter types within the tree, e.g., by selecting parameter types for upper level coarse tuning. For example, the stimulation parameter types may be arranged so that higher priority adjustments occur at higher levels of the tree and lower priority adjustments occur at lower levels of the tree. In particular, the parameters may be prioritized so that parameters believed to have the largest impact on efficacy are placed in upper levels of the tree, while parameters having lesser impacts are placed in lower levels of the tree. For example, one level of the tree may contain nodes that represent adjustments to pulse rate, while another level of the tree contains nodes that represent adjustments to pulse width, and yet another level contains nodes that represent adjustments in pulse amplitude.

In one example, the first level contains nodes specifying electrode configurations, the second level contains nodes specifying pulse rates, the third level contains nodes specifying pulse widths, and the fourth level contains nodes specifying voltage amplitudes. Hence, in this example, electrode configuration are prioritized first as having the greatest impact on efficacy, followed by pulse rate, pulse width and amplitude, all taken relative to the initial set of stimulation parameters However, more or less levels may be included in the therapeutic tree. Generally, stimulation parameter types that provide a greater change in stimulation are located near the first or second levels of the therapeutic tree, or higher in the tree, to provide coarse tuning. Parameter types that provide fine tuning are located at lower levels of the therapeutic tree. Stimulation parameter types not included in the therapeutic tree may be set to a default value by the factory or the clinician. In some embodiments, stimulation parameter types not included in the therapeutic tree may be added to the therapeutic tree if effective stimulation therapy is not defined by the stimulation parameter types originally included in the tree.

External programmer 20 may be a clinician programmer or a patient programmer. In some embodiments, external programmer 20 may be a computer connected to a network, where the programmer consults a network server to evaluate therapy efficacy and create a program path with the therapeutic tree. In the case where external programmer 20 is not connected to a network, the programmer includes the therapeutic tree in a memory such that the clinician may use the programmer to create or modify a program path at any time. If a new program path is created, the stimulation parameters, or nodes, of the new program path are transmitted to stimulator 14 to define the new stimulation therapy. External programmer 20 may retain all used programs in a memory so that the clinician can review the delivered therapies. In some embodiments, used and ineffective program paths may be removed from the therapeutic tree help guide the clinician and patient 12 to find an effective program path.

In other embodiments, a memory of stimulator 14 may store all data associated with the therapeutic tree and used program paths. External programmer 20 retrieves data from stimulator 14 to allow the clinician or patient 12 to create a program path. In this manner, all data is retained within patient 12 and multiple external programmers 24 may be used to treat the patient without storing private patient data away from the patient.

While the clinician or patient 12 may desire to manually create a program path for stimulation therapy, system 10 may provide automatic program path creation based upon the entered patient feedback. Depending on the efficacy of the current therapy, external programmer 20 may determine that the therapy is not "good enough" based upon certain criteria. In some embodiments, patient 12 may indicate how much the pain has been reduced through stimulation via a rating system. For example, patient 12 may enter a numerical rating on a scale of 1 to 10, with 10 indicating the pain is completely gone, and 1 indicating that the pain has not been noticeably reduced. Other examples may include graphical rating systems and descriptive words selected from a list, and other methods of indicating efficacy of the therapy.

In some cases, patient 12 may indicate the efficacy of the stimulation therapy indirectly by providing some other type of input. For example, when stimulation is not efficacious, a patient may increase the amplitude or change other stimulation parameters in an attempt to improve the stimulation efficacy. Stimulators or programmers according to the invention may track the frequency and type of programming changes, and use such information as feedback for evaluating the efficacy of the stimulation.

In addition, patient 12 may provide medication input to indicate the dosage and frequency of pain medication taken to reduce pain symptoms. Increased pain medication taken by patient 12 may indicate that current stimulation therapy is not effective at reducing pain symptoms. Conversely, little or no pain medication taken by patient 12 may indicate efficacious stimulation treatment.

Furthermore, sensors may be used to detect physiological parameters that can indicate if the stimulation therapy is efficacious. In addition to using such information as efficacy feedback, stimulators or programmers may invoke tree-based programming based on therapy adjustment, medication input, or sensors signals, which may act as an indication that the stimulation therapy requires improvement. The use of a tree-based structure to improve stimulation efficacy may occur periodically, continuously, or as requested or needed throughout chronic therapy.

In cases where the therapy efficacy is very low, external programmer 20 may automatically move up several levels of the therapeutic tree to more quickly change the stimulation therapy. If the therapy is close to being very effective, external programmer 20 may only move to a different node within the same level of the tree. The therapeutic tree enables system 10 to include a feedback loop with variable instructions based upon the efficacy feedback, which may allow patient 12 to find the most efficacious therapy in a shorter amount of time.

In some embodiments, stimulator 14 may be used in a trial mode to evaluate the efficacy of electrical stimulation. In a trial mode, finding the most effective therapy may not be necessary to prove that stimulation therapy is effective in treating patient 12. External programmer 20 may attempt to find a program path that provides a minimal amount of therapy, e.g., a 50 percent efficacy improvement determination, and stop modifying the therapy with the therapeutic tree. In this manner, the clinician may quickly prove reasonable therapy efficacy without the risk of further modifications to the therapy that may reduce the therapy efficacy. After the trial mode is over, external programmer 20 may resume creating new program paths in the therapeutic tree when deemed necessary from the feedback of patient 12.

Figure 2:
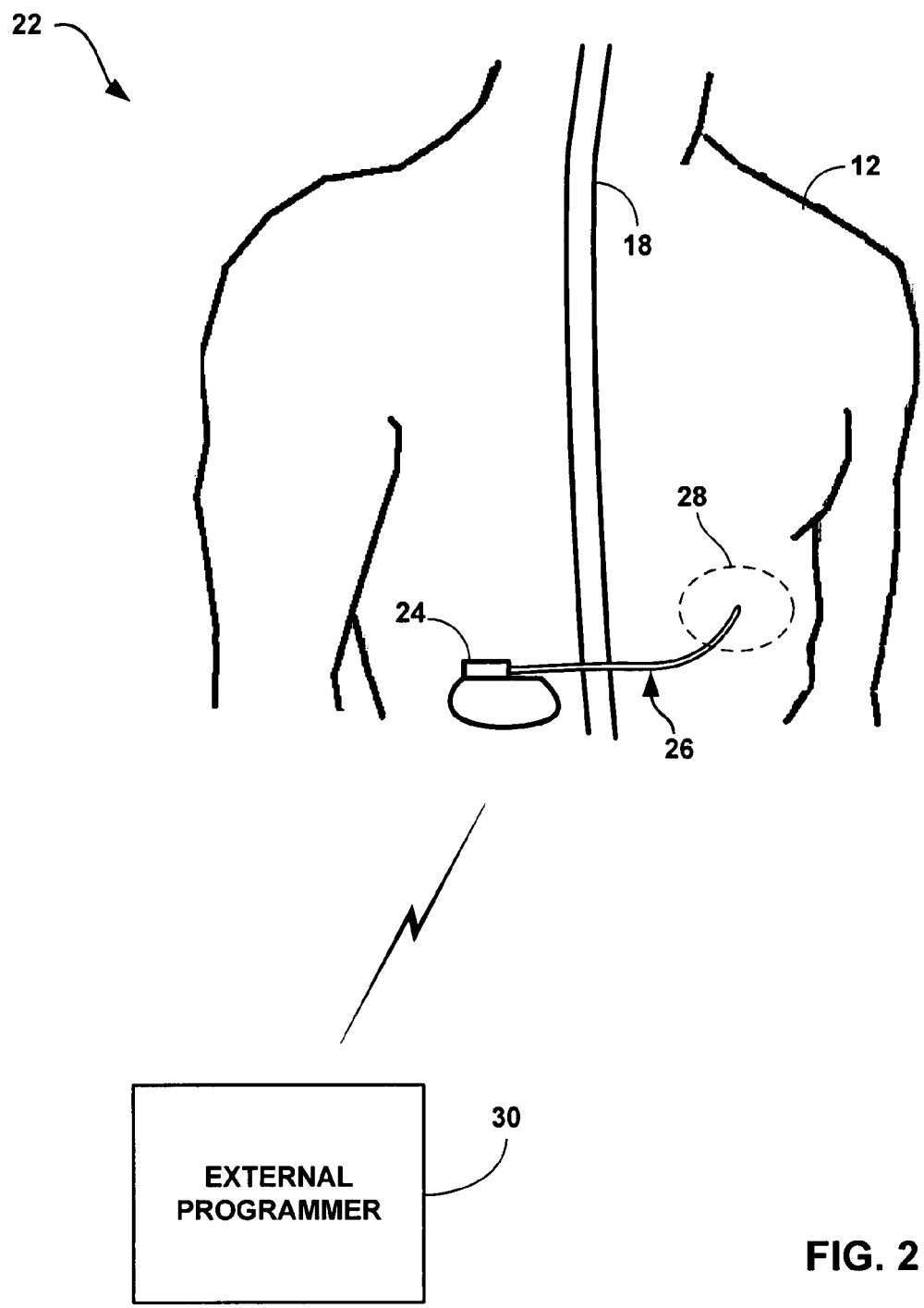
FIG. 2 is a schematic diagram illustrating an implantable peripheral nerve stimulation system that utilizes a therapeutic tree for programming stimulation therapy.

FIG. 2 is a schematic diagram illustrating an implantable peripheral nerve field stimulation system that incorporates a therapeutic tree for programming stimulation therapy. As shown in FIG. 2, system 22 includes implantable stimulator 24 and external programmer 30 shown in conjunction with a patient 12. System 22 is similar to system 10 of FIG. 1 in using a therapeutic tree to program stimulation therapy. However, system 22 is directed to providing peripheral nerve field stimulation (PNFS) to region 28 of patient 12. Stimulation pulses are delivered to region 28 of patient 12 via one or more electrodes of lead 26, where the electrode is placed adjacent to the target tissue. In the example of FIG. 2, stimulation pulses are delivered to region 28 to reduce the amount of pain perceived by patient 12 at the region. The PNFS may be delivered to region 28 in addition stimulation at other regions of patient 12, such as SCS. Region 28 may include nerves which innervate skeletal muscles, skin, and other surrounding tissues. Pain may emanate from these tissues, and stimulation of the nerves in region 28 may reduce or eliminate the pain in and around region 28. In some examples, multiple leads may be coupled to stimulator 24 to deliver stimulation therapy to multiple regions of patient 12.

With reference to FIG. 2, a user, such as a clinician or patient 12, may interact with a user interface of external programmer 30 (similar to external programmer 20) to provide system 22 with feedback indicating the efficacy of the stimulation pulses. Based on the efficacy feedback from the user, the therapeutic tree (not shown) is used to guide programming of the stimulation therapy for peripheral nerve stimulation. In particular, the efficacy feedback directs programming through selected branches of the tree to identify a program providing desirable efficacy.

Stimulator 24 may be implanted in patient 12 at a location minimally noticeable to the patient. For PNFS, stimulator 24 may be located in the lower abdomen, lower back, or other locations. Lead 26 is tunneled from stimulator 24 through tissue to reach the target tissue of region 28 for stimulation delivery. At the distal tip of lead 26 are one or more electrodes (not shown) that transfer the stimulation pulses from the lead to the tissue. Lead 26 and the electrodes thereon may take the form of any of the examples discussed above with reference to lead 16.

The target tissue may be any tissue affected by electrical pulses within region 28. Such tissue may include peripheral nerves, smooth muscle, skeletal muscle, and skin. Stimulation of region 28 may prevent pain signals from traveling to the spinal cord and on to the brain of the patient. Patient 12 perceives the lack of pain signals as a reduction in pain and an efficacious therapy.

Figure 3:
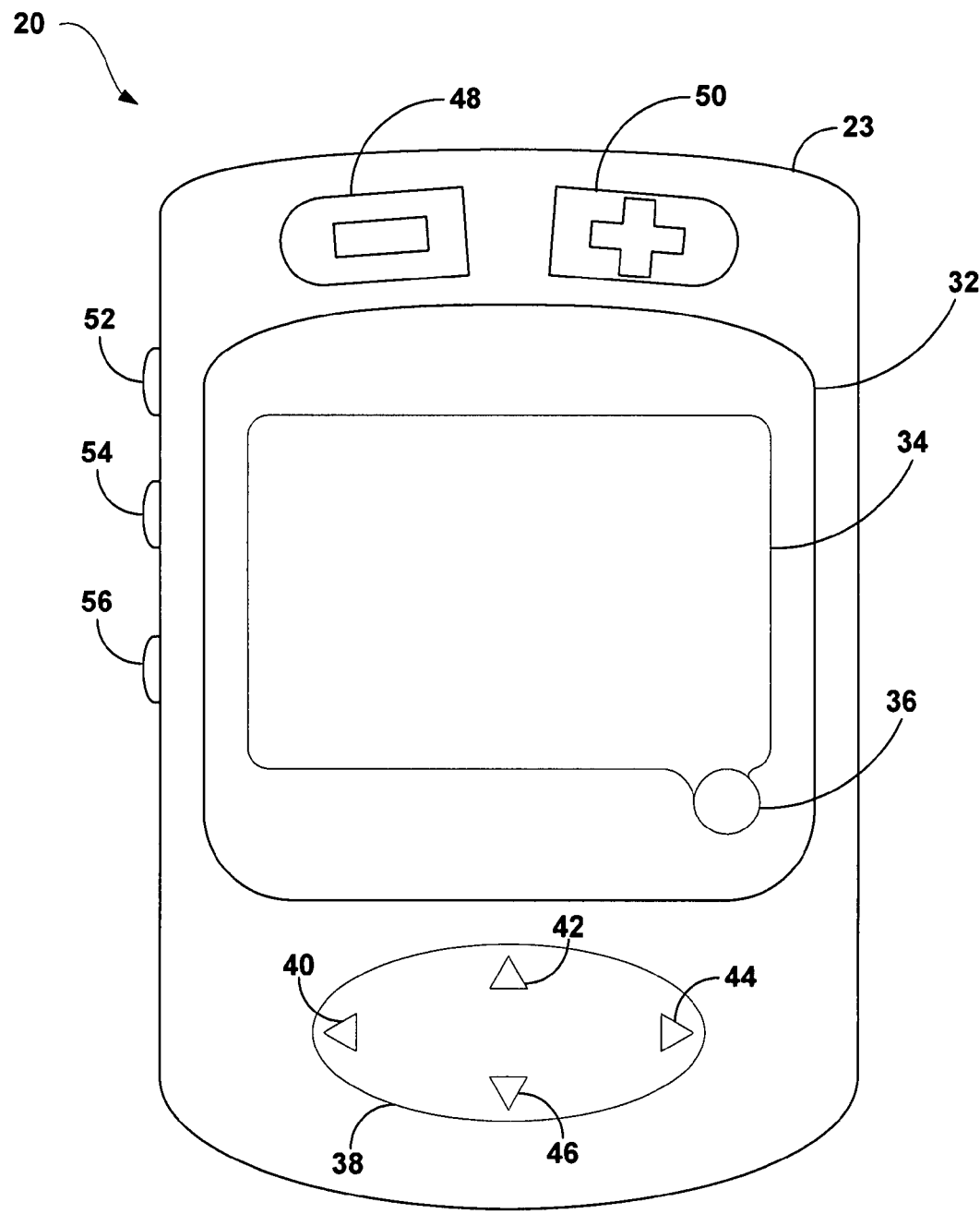
FIG. 3 is a schematic diagram illustrating an example external programmer for programming stimulation therapy.

FIG. 3 is a schematic diagram illustrating an example external programmer for programming stimulation therapy. As shown in FIG. 3, external programmer 20 provides a user interface for a user, such as patient 12, to manage and program stimulation therapy. Programmer 20 is described in FIG. 3, but programmer 30 may also be described in a similar manner. Programmer 20 is protected by housing 23 which encloses circuitry necessary for the programmer to operate. Programmer 20 also includes display 34, power button 56, increase button 50, decrease button 48, backlight 36, and select buttons 52 and 54. Cover 32 protects screen 34 from being damaged during programmer 20 use. Programmer 20 also includes control pad 38 which allows a user to navigate through items displayed on display 34 in the direction of arrows 40, 42, 44 and 46. In some embodiments, the buttons and pad may take the form of soft keys, whose functionality may change, for example, based on the current programming operation or user preference.

In the illustrated embodiment, programmer 20 is a hand held device. Programmer 20 may be a patient programmer that may accompany patient 12 at all times. In some cases, programmer 20 may be used by a clinician when patient 12 visits the clinician. In other embodiments, programmer 20 may be a clinician programmer that remains with the clinician or in the clinic, and is used by the clinician and/or patient 12 when in the patient is in the clinic.

Housing 23 may be constructed of a polymer, metal alloy, composite, or combination material suitable to protect and contain components of programmer 20. In addition, housing 23 may be partially or completely sealed such that fluids, gases, or other elements may not penetrate the housing and affect components therein. Power button 56 may turn programmer 20 on or off as desired by patient 12. Backlight 36 may also control the illumination level, or backlight level, of display 34. In some embodiments, backlight 36 may be a knob that rotates clockwise and counter-clockwise to control programmer 20 operational status and display 34 illumination. Programmer 20 is prevented from turning off during telemetry with stimulator 14 or another device to prevent the loss of transmitted data or the stalling of normal operation. Alternatively, programmer 20 and stimulator 14 may include instructions which handle possible unplanned telemetry interruption, such as battery failure or inadvertent device shutdown.

Display 34 may be a liquid crystal display (LCD) or similar monochrome or color display capable of providing information, such as a user interface, to patient 12. Display 34 may provide a user interface regarding current stimulation therapy, a therapeutic tree for programming stimulation therapy, receiving feedback or medication input from patient 12, an active group of stimulation programs, and operational status of programmer 20. Control pad 38 allows patient 12 to navigate through items displayed on display 34. Patient 12 may press control pad 38 on any of arrows 40, 42, 44, and 46 in order to move to another item on display 34 or move to another screen not currently shown on the display. In some embodiments, pressing the middle of control pad 38 may select any item highlighted in display 34. In other embodiments, scroll bars, a touch pad, scroll wheel, individual buttons, or a joystick may perform the complete or partial function of control pad 38.

Decrease button 48 and increase button 50 provide an input mechanism for patient 12. In general, decrease button 48 may decrease the value of a highlighted stimulation parameter every time the decrease button is pressed. In contrast, increase button 50 may increase the value of a highlighted stimulation parameter one step every time the increase button is pressed. While buttons 48 and 50 may be used to control the value of any stimulation parameter, buttons 48 and 50 may also control patient feedback input. For example, pressing increase button 50 may be efficacy input indicating that the current stimulation program is reducing pain. Conversely, pressing decrease button 48 may be efficacy input indicating that the current stimulation program is not reducing pain. In other embodiments, decrease button 48 and increase button 50 may only decrease and increase stimulation parameters while control pad 38 is used to receive efficacy feedback from patient 12 or a clinician.

Select buttons 42 and 44 may be configured to perform operational functions related to stimulation therapy or the use of programmer 20. For example, buttons 42 and 44 may control the volume of audible sounds produced by programmer 20, wherein button 42 increases the volume and button 44 decreases the volume. Button 46 may be pressed to enter an operational menu that allows patient 12 to configure the user interface of programmer 20 to the desires of patient 12. For example, patient 12 may be able to select a language, backlight delay time, display 24 brightness and contrast, or other similar options. In alternative embodiments, buttons 38 and 40 may control all operational and selection functions, such as those related to audio volume or stimulation therapy.

Programmer 20 may take other shapes or sizes not described herein. For example, programmer 20 may take the form of a clam-shell shape, similar to cellular phone designs. When programmer 20 is closed, some or all elements of the user interface may be protected within the programmer. When programmer 20 is opened, one side of the programmer may contain a display while the other side may contain input mechanisms. In any shape, programmer 20 may be capable of performing the requirements described herein. Alternative embodiments of programmer 20 may include other input mechanisms such as a keypad, microphone, camera lens, or any other input media that allows the user to interact with the user interface provided by programmer 20.

In alternative embodiments, the buttons of programmer 20 may perform different functions than the functions provided in FIG. 3 as an example. In addition, other embodiments of programmer 20 may include different button layouts or number of buttons. For example, programmer 20 may even include a single touch screen that incorporates all user interface functionality.

Figure 4:
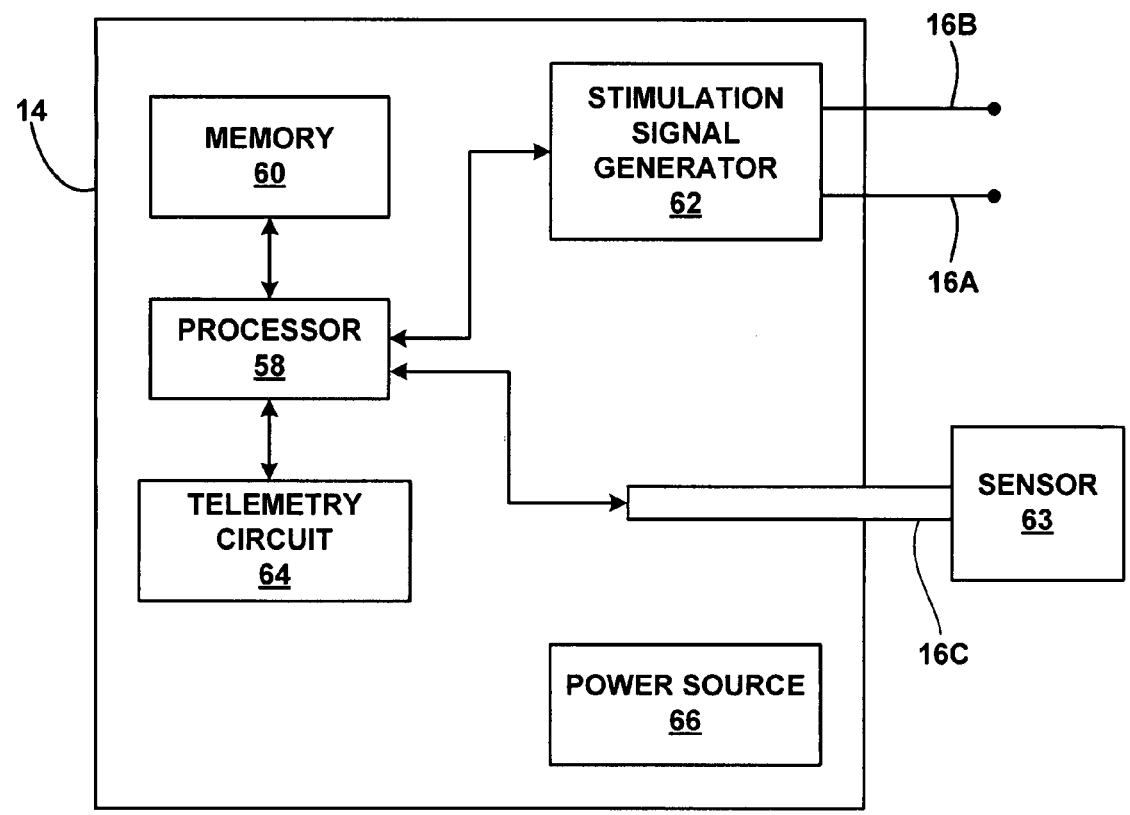
FIG. 4 is a functional block diagram illustrating various components of an implantable stimulator that communicates wirelessly with an external programmer.

FIG. 4 is a functional block diagram illustrating various components of an implantable stimulator, which may communicate wirelessly with an external programmer. In the example of FIG. 4, stimulator 14 includes a processor 58, memory 60, stimulation signal generator 62, sensor 63, telemetry circuit 64, and power source 66. Memory 60 may store instructions for execution by processor 58, stimulation therapy data, efficacy feedback, and any other information regarding therapy or patient 12. Therapy information may be recorded for long-term storage and retrieval by a user, and adjustment of the program path of the therapeutic tree. Memory 60 may include separate memories for storing instructions, the therapeutic tree, program path, and program histories.

Processor 58 controls stimulation signal generator 62 to deliver electrical stimulation therapy via one or more leads 16. An exemplary range of neurostimulation stimulation parameters likely to be effective in treating chronic pain, e.g., when applied to spinal cord 18, are listed below. While stimulation pulses are described, stimulation signals may be of any forms such as sine waves or the like.

1. Frequency: between approximately 0.5 Hz and 2000 Hz, more preferably between approximately 30 Hz and 250 Hz, and still more preferably between approximately 60 Hz and 150 Hz.

2. Amplitude: between approximately 0.1 volts and 60 volts, more preferably between approximately 0.5 volts and 20 volts, and still more preferably between approximately 1 volt and 10 volts. In other embodiments, a current amplitude may be defined as the biological load in the voltage is delivered.

3. Pulse Width: between about 10 microseconds and 5000 microseconds, more preferably between approximately 100 microseconds and 1000 microseconds, and still more preferably between approximately 180 microseconds and 450 microseconds.

In some embodiments, processor 58 modifies the current program path or stimulation parameters stored in memory 60 based on traversal of the therapeutic tree and efficacy feedback using the techniques described herein. In some embodiments, another device, such as programmer 20, 30, modifies the current program path or stimulation parameters stored in memory 60 based on traversal of the therapeutic tree and efficacy feedback. In such embodiments, processor 58 may receive modification of the stimulation parameters from the other device via telemetry circuit 64, and store the modified stimulation parameters in memory 60.

In either case, processor 58 controls stimulation signal generator 62 to provide electrical stimulation according to the stimulation parameters stored in memory 60, which may be determined based on the current program path of the therapeutic tree. Processor 58 may determine that a new program path should be created, among other reasons, based on information regarding the operation of electrodes and the leads 16.

If one or more electrodes becomes damaged or inoperable, processor 58 may eliminate a particular node from the therapeutic tree, or indicate to another device via telemetry circuit 64 that a particular node should be removed from the tree. If the damaged electrode is used by the current program, processor 58 or another device may select an electrode configuration or combination node nearest the current program path of the therapeutic tree, or stop stimulation until a new program path is determined with efficacy feedback from patient 12, the clinician, or a sensor.

Processor 58 may include a microprocessor, a controller, a digital signal processor (DSP), an application specific integrated circuit (ASIC), a field-programmable gate array (FPGA), discrete logic circuitry, or the like. Memory 60 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 60 stores program instructions that, when executed by processor 58, cause stimulator 14 and processor 58 to perform the functions attributed to them herein.

In some embodiments, the therapeutic tree may be traversed based on subjective efficacy feedback received from a patient or clinician, or feedback regarding stimulation adjustments or medication usage. Processor 58 may additionally or alternatively receive measurements or signals from sensor 63 that are indicative of one or more physiological parameters of patient 12. Such physiological parameter measurements or signals may be used by processor 58 or other devices, such as a programmer 20, 30, as objective efficacy feedback for traversal of the therapeutic tree.

Sensor 63 generates a signal as a function of one or more physiological parameters of a patient 12. Stimulator 14 may include circuitry (not shown) that conditions the signals generated by sensors 63 such that they may be analyzed by processor 58. For example, stimulator 14 may include one or more analog to digital converters to convert analog signals generated by sensor 63 into digital signals usable by processor 58, as well as suitable filter and amplifier circuitry. Although shown as including one sensor 63, system 10 may include any number of sensors.

Further, as illustrated in FIG. 4, sensor 63 may be included as part of stimulator 14, or coupled to the stimulator via lead 16C, which may or may not include electrodes for delivering stimulation. In some embodiments, a sensor 63 located outside of stimulator 14 may be in wireless communication with processor 58. Wireless communication between sensor 63 and stimulator 14 may, as examples, include radio frequency (RF) communication or communication via electrical signals conducted through the tissue and/or fluid of a patient 12.

A variety of physiological parameters of patient 12 may vary based upon the pain experienced by the patient, and thus based upon the efficacy of the stimulation delivered by stimulator 14. Accordingly, signals generated by one or more sensors 63 may reflect the pain state of patient and efficacy of stimulation. One or more components of a system 10, 22 according to the invention may monitor signals generated by sensors 63 as efficacy feedback for the purpose of traversing a therapeutic tree to identify efficacious stimulation parameters according to the techniques described herein.

Example physiological parameters of patient 12 that may be monitored by a stimulator 14 via one or more sensors 63 include activity, posture, heart rate, electrocardiogram (ECG) morphology, respiration rate, respiratory volume, blood pressure, blood oxygen saturation, partial pressure of oxygen within blood, partial pressure of oxygen within cerebrospinal fluid (CSF), muscular activity and tone, core temperature, subcutaneous temperature, arterial blood flow, the level of melatonin within one or more bodily fluids, brain electrical activity, and eye motion. Further, in some external medical device embodiments of the invention, galvanic skin response may additionally or alternatively be monitored. Sensor 63 may be of any type known in the art capable of generating a signal as a function of one or more of these parameters.

The activity level of patient 12 may vary based on the pain experienced by the patient. A patient in pain may avoid activity and, conversely, as pain is alleviated may engage in greater activity. Accordingly, the activity level of patient 12 may indicate the efficacy of stimulation used to treat pain, and may be used as efficacy feedback for traversal of a therapeutic tree according to the techniques described herein.

Stimulator 14 may include one or more sensors 63 that generate a signal as a function of patient activity. For example, sensors 63 may include one or more accelerometers, gyros, mercury switches, or bonded piezoelectric crystals that generates a signal as a function of patient activity, e.g., body motion, footfalls or other impact events, and the like. Additionally or alternatively, sensors 63 may include one or more electrodes that generate an electromyogram (EMG) signal as a function of muscle electrical activity, which may indicate the activity level of a patient. The electrodes may be, for example, located in the legs, abdomen, chest, back or buttocks of a patient 12 to detect muscle activity associated with walking, running, or the like. The electrodes may be coupled to stimulator 14 wirelessly or by leads 16 or, if stimulator 14 is implanted in these locations, integrated with a housing of stimulator 14.

However, bonded piezoelectric crystals located in these areas generate signals as a function of muscle contraction in addition to body motion, footfalls or other impact events. Consequently, use of bonded piezoelectric crystals to detect activity of a patient 12 may be preferred in some embodiments in which it is desired to detect muscle activity in addition to body motion, footfalls, or other impact events. Bonded piezoelectric crystals may be coupled to stimulator 14 wirelessly or via leads 16, or piezoelectric crystals may be bonded to the can of stimulator 14 when the stimulator is implanted in these areas, e.g., in the back, chest, buttocks or abdomen of a patient 12. Processor 58 may also detect spasmodic or pain related muscle activation via the signals generated by such sensors.

In some embodiments, the activity level of a patient may be determined by monitoring another physiological parameter that varies as a function of patient activity. For example, sensor 63 may include electrodes located on leads or integrated as part of the housing of stimulator 14 that generate an electrogram signal as a function of electrical activity of the heart of a patient 12, and processor 58 may monitor the heart rate of the patient 12 based on the electrogram signal. In other embodiments, a sensor 63 may include an acoustic sensor within stimulator 14, a pressure or flow sensor within the bloodstream or cerebrospinal fluid of a patient 12, or a temperature sensor located within the bloodstream of the patient 12. The signals generated by such sensors may vary as a function of contraction of the heart of a patient 12, and can be used by processor 58 to monitor the heart rate of the patient 12.

In some embodiments, processor 58 may detect, and measure values for one or more ECG morphological features within an electrogram generated by electrodes as described above. ECG morphological features may vary based on patient activity. For example, the amplitude of the ST segment of the ECG may increase as patient activity increases. Further, the amplitude of a QRS complex or T-wave may increase, and the widths of the QRS complex and T-wave may decrease as patient activity increases.

Additionally, the respiration rate and volume of patient 12 increase with increasing activity by the patient. In some embodiments, sensor 63 may include an electrode pair, including one electrode integrated with the housing of stimulator 14 and one of the electrodes of leads 16, that generates a signal as a function of the thoracic impedance of a patient 12, which varies as a function of respiration by the patient 12. In other embodiments, sensor 63 may include a strain gauge, bonded piezoelectric element, or pressure sensor within the blood or cerebrospinal fluid that generates a signal that varies based on patient respiration. An electrogram generated by electrodes as discussed above may also be modulated by patient respiration, and may be used as an indirect representation of respiration rate or volume.

Sensor 63 may include any of a variety of known temperature sensors to generate a signal as a function of a core or subcutaneous temperature of a patient 12, which varies based on patient activity. Such electrodes and temperature sensors may be incorporated within the housing of stimulator 14, or coupled to the stimulator wirelessly or via leads. Sensor 63 may also include a pressure sensor within, or in contact with, a blood vessel. The pressure sensor may generate a signal as a function of the a blood pressure of a patient 12, which varies based on patient activity, and may, for example, comprise a Chronicle Hemodynamic Monitor™ commercially available from Medtronic, Inc. of Minneapolis, Minn.

Sensor 63 may also include optical pulse oximetry sensors or Clark dissolved oxygen sensors located within, as part of a housing of, or outside of stimulator 14, which generate signals as a function of blood oxygen saturation and blood oxygen partial pressure respectively. In some embodiments, a system 10 may include a catheter with a distal portion located within the cerebrospinal fluid of a patient 12, and the distal end may include a Clark dissolved oxygen sensor to generate a signal as a function of the partial pressure of oxygen within the CSF. Blood oxygen saturation, and blood or CSF oxygen partial pressure, vary based on patient activity.

In some embodiments, sensor 63 may include one or more intraluminal, extraluminal, or external flow sensors positioned to generate a signal as a function of arterial blood flow, which varies based on patient activity level. A flow sensor may be, for example, an electromagnetic, thermal convection, ultrasonic-Doppler, or laser-Doppler flow sensor. Further, in some external medical device embodiments of the invention, sensor 63 may include one or more electrodes positioned on the skin of a patient 12 to generate a signal as a function of galvanic skin response, which reflects patient activity level.

When a patient is in pain, the patient may avoid particular postures, or transition between postures as a result of activity less frequently. Accordingly, posture and frequency of posture transitions of patient 12 may reflect the efficacy of stimulation therapy delivered by stimulator 14 to treat pain, and may be used as efficacy feedback for traversal of a therapeutic tree according to the techniques described herein.

In some embodiments, sensor 63 may include a plurality of accelerometers, gyros, or magnetometers oriented orthogonally that generate signals which indicate the posture of a patient 12. In addition to being oriented orthogonally with respect to each other, sensor 63 is used to detect the posture of a patient 12 may be generally aligned with an axis of the body of the patient 12. In exemplary embodiments, stimulator 14 includes three orthogonally oriented posture sensors 63.

When sensor 63 include accelerometers, for example, that are aligned in this manner, processor 58 may monitor the magnitude and polarity of DC components of the signals generated by the accelerometers to determine the orientation of a patient 12 relative to the Earth's gravity, e.g., the posture of the patient 12. In particular, the processor 58 may compare the DC components of the signals to respective threshold values stored in memory 60 to determine whether a patient 12 is or is not recumbent. Further information regarding use of orthogonally aligned accelerometers to determine patient posture may be found in a commonly assigned U.S. Pat. No. 5,593,431, which issued to Todd J. Sheldon.

Another sensor 63 that may generate a signal that indicates the posture of a patient 12 include electrodes that generate an electromyogram (EMG) signal, or bonded piezoelectric crystals that generate a signal as a function of contraction of muscles. Such sensor 63 may be implanted in the legs, buttocks, abdomen, or back of a patient 12, as described above. The signals generated by such sensors when implanted in these locations may vary based on the posture of a patient 12, e.g., may vary based on whether the patient is standing, sitting, or lying down.

Further, the posture of a patient 12 may affect the thoracic impedance of the patient. Consequently, sensor 63 may include an electrode pair, including one electrode integrated with the housing of an stimulator 14 and one of electrodes on leads 16, that generates a signal as a function of the thoracic impedance of the patient 12, and processor 58 may detect the posture or posture changes of the patient 12 based on the signal. The electrodes of the pair may be located on opposite sides of the patient's thorax. For example, the electrode pair may include one of the electrodes located proximate to the spine of a patient for delivery of SCS therapy, and stimulator 14 with an electrode integrated in its housing may be implanted in the abdomen of a patient 12.

Additionally, changes of the posture of a patient 12 may cause pressure changes with the CSF of the patient. Consequently, sensor 63 may include pressure sensors coupled to one or more intrathecal or intracerebroventricular catheters, or pressure sensors coupled to stimulator 14 wirelessly or via any of leads 16. CSF pressure changes associated with posture changes may be particularly evident within the brain of the patient, e.g., may be particularly apparent in an intracranial pressure (ICP) waveform.

In addition to activity level and posture, the quality of sleep experienced by patient 12 may reflect the extent of experienced pain and stimulation efficacy. More particularly, pain may negatively affect the quality of sleep experienced by patient 12.

In some embodiments, to monitor sleep quality as efficacy feedback, processor 58 may identify when a patient 12 is attempting to sleep and/or asleep. For example, processor 58 may identify the time that patient begins attempting to fall asleep based on an indication received from a patient 12, e.g., via programmer 20, 30 and a telemetry circuit 64. In other embodiments, processor 58 identifies the time that a patient 12 begins attempting to fall asleep, falls asleep and/or wakes up based on the activity level, posture, or other physiological parameters of the patient 12.

In order to determine when patient 12 is attempting to sleep and asleep, processor 58 may identify a time when the activity level of a patient 12 falls below a threshold activity level value stored in memory 60, and may determine whether the activity level remains substantially below the threshold activity level value for a threshold amount of time stored in memory 60. In other words, a patient 12 remaining inactive for a sufficient period of time may indicate that patient 12 is attempting to fall asleep. If processor 58 determines that the threshold amount of time is exceeded, processor 58 may identify the time at which the activity level fell below the threshold activity level value as the time that a patient 12 began attempting to fall asleep. Furthermore, processor 58 may determine when patient 12 awakes based on the activity level exceeding a threshold level, or exceeding the threshold level for a threshold period of time. Such thresholds may be stored in memory 60.

In some embodiments, processor 58 determines whether a patient 12 is attempting to fall asleep, asleep, or awake based on whether the patient 12 is or is not recumbent, e.g., lying down, using posture sensors 63 as described above. In some embodiments, processor 58 considers both the posture and the activity level of patient 12 when determining whether a patient 12 is attempting to fall asleep or is asleep. For example, processor 58 may determine whether a patient 12 is attempting to fall asleep based on a sufficiently long period of sub-threshold activity, as described above, and may identify the time that patient began attempting to fall asleep as the time when a patient 12 became recumbent. Any of a variety of combinations or variations of these techniques may be used to determine when a patient 12 is attempting to fall asleep, and a specific one or more techniques may be selected based on the sleeping and activity habits of a particular patient.

In other embodiments, processor 58 determines when a patient 12 is attempting to fall asleep based on the level of melatonin in a bodily fluid. In such embodiments, sensor 63 may take the form of a chemical sensor that is sensitive to the level of melatonin or a metabolite of melatonin in the bodily fluid, and estimate the time that a patient 12 will attempt to fall asleep based on the detection. For example, processor 58 may compare the melatonin level or rate of change in the melatonin level to a threshold level stored in memory 60, and identify the time that threshold value is exceeded. Processor 58 may identify the time that a patient 12 is attempting to fall asleep as the time that the threshold is exceeded, or some amount of time after the threshold is exceeded.

Processor 58 may also determine when a patient 12 is asleep based on other physiological parameters sensed by one or more sensors 63. Detected values of physiological parameters of a patient 12, such as heart rate, ECG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response may discernibly change when a patient 12 falls asleep or awakes. Some of these physiological parameters may be at low values when a patient 12 is asleep. Further, the variability of at least some of these parameters, such as heart rate and respiration rate, may be at a low value when the patient is asleep.

Consequently, in order to detect when a patient 12 falls asleep and wakes up, processor 58 may monitor one or more of these physiological parameters, or the variability of these physiological parameters, and detect the discernable changes in their values associated with a transition between a sleeping state and an awake state. In some embodiments, processor 58 may determine a mean or median value for a parameter based on values of a signal over time, and determine whether a patient 12 is asleep or awake based on the mean or median value. Processor 58 may compare one or more parameter or parameter variability values to thresholds stored in memory 60 to detect when a patient 12 falls asleep or awakes. The thresholds may be absolute values of a physiological parameter, or time rate of change values for the physiological parameter, e.g., to detect sudden changes in the value of a parameter or parameter variability. In some embodiments, a threshold used by processor 58 to determine whether a patient 12 is asleep may include a time component. For example, a threshold may require that a physiological parameter be above or below a threshold value for a period of time before processor 58 determines that patient is awake or asleep.

Additionally, in some embodiments, sensor 63 may include one or more electrodes positioned within or proximate to the brain of patient, which detect electrical activity of the brain. For example, in embodiments in which stimulator 14 delivers stimulation to the brain, processor 58 may be coupled to electrodes implanted on or within the brain via leads 16. Processor 58 may determine whether patient is asleep or awake based on the electrical activity of the brain of patient 12, e.g., an electroencephalogram (EEG) of patient 12, detected by such sensors 63. Furthermore, processor 58 may determine within which sleep state, e.g., S1-S4 or rapid eye movement (REM), patient 12 is based on the EEG or any one or more of the other physiological parameters discussed above.

Processor 58, or another device in systems 10, 22, may determine values for any of a variety of metrics indicative of sleep quality based on identification of when patient 12 is attempting to sleep, asleep, within particular sleep states, or awake. Such sleep quality metrics may be used by processor 58 or another device as efficacy feedback for traversal of a therapeutic tree and identification of stimulation parameter values. As examples, processor 58 may determine the amount or percentage of time asleep or in particular sleep states, the length or frequency of arousals or other disturbances during sleep, the length of time attempting to sleep prior to falling asleep (sleep latency), or the percentage of time asleep when attempting to sleep (sleep efficiency). Sensor 63 may be any of the sensors, and processor 58 may monitor any of physiological parameters and determine any of the sleep quality metrics described in commonly-assigned and co-pending application Ser. No. 11/691,376, by Miesel et al., entitled "COLLECTING SLEEP QUALITY INFORMATION VIA A MEDICAL DEVICE," filed Mar. 26, 2007, the entire content of which is incorporated herein by reference.

Processor 58, or another device in systems 10, 22, may determine values for any of a variety of metrics indicative of activity level, posture, or posture transitions based on the physiological parameters and sensor 63 signals discussed above. Such activity and posture metrics may be used by processor 58 or another device as efficacy feedback for traversal of a therapeutic tree and identification of stimulation parameter values. Sensor 63 may be any of the sensors, and processor 58 may monitor any of physiological parameters and determine any of the posture and activity metrics described in commonly-assigned and co-pending application Ser. No. 11/691,411, by Miesel et al., entitled "COLLECTING ACTIVITY INFORMATION TO EVALUATE THERAPY;" and commonly-assigned and co-pending application Ser. No. 11/691,391, by Miesel et al., entitled "COLLECTING POSTURE INFORMATION TO EVALUATE THERAPY. Both of these applications were filed on Mar. 26, 2007, and their entire content is incorporated herein by reference.

In some examples, processor 58 may be able to manage the power consumption of stimulation therapy using a therapeutic tree. Each node in the therapeutic tree may be weighted according to power usage values, which is a system performance value, for the particular parameter of the node. Alternatively, a second therapeutic tree may be used after identifying a program path in the first therapeutic tree in order to optimize the power consumption of the stimulation therapy. In either case, the therapeutic tree may be used to weight and organize power usage values to minimize the consumption of power during therapy. For example, once an electrode configuration is selected, the levels of the therapeutic tree may continue from pulse rate, to pulse width, to amplitude.

Wireless telemetry in stimulator 14 with external programmer 20 or another device may be accomplished by RF communication or proximal inductive interaction of stimulator 14 with external programmer 20. Accordingly, telemetry circuit 64 may send information to external programmer 20 on a continuous basis, at periodic intervals, or upon request from the implantable stimulator or programmer. Wireless telemetry may be accomplished by RF communication or proximal inductive interaction of stimulator 14 with external programmer 20.

Power source 66 delivers operating power to the components of stimulator 14. Power source 66 may include a small rechargeable or non-rechargeable battery and a power generation circuit to produce the operating power. Recharging may be accomplished through proximal inductive interaction between an external charger and an inductive charging coil within stimulator 14. In some embodiments, power requirements may be small enough to allow stimulator 14 to utilize patient motion and implement a kinetic energy-scavenging device to trickle charge a rechargeable battery. In other embodiments, traditional batteries may be used for a limited period of time. As a further alternative, an external inductive power supply could transcutaneously power stimulator 14 whenever measurements are needed or desired.

Figure 5:
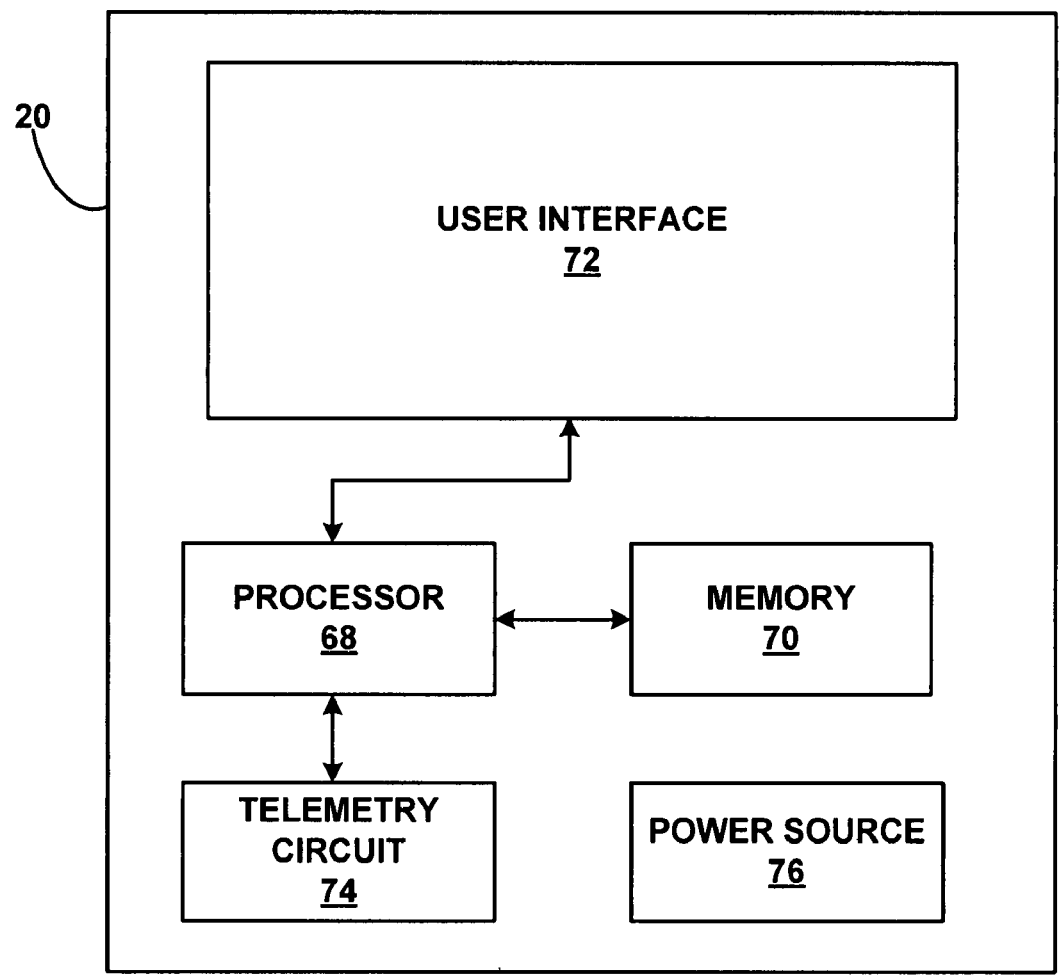
FIG. 5 is a functional block diagram illustrating various components of an external programmer that communicates wirelessly with the implantable stimulator.

FIG. 5 is a functional block diagram illustrating various components of an external programmer that communicates wirelessly with the implantable stimulator. As shown in FIG. 5, external programmer 20 includes processor 68, memory 70, telemetry circuit 74, user interface 72, and power source 76. The clinician or patient 12 interacts with user interface 72 in order to manually change the program path, adjust voltage or current amplitude, or other stimulation parameters, change weighting (i.e., prioritization or level) of stimulation parameter types within the therapeutic tree, provide efficacy feedback, or view stimulation data.

User interface may include a screen and one or more input buttons that allow external programmer 20 to receive input from a user. The screen may be a liquid crystal display (LCD), dot matrix display, or touch screen. The input buttons may include a touch pad, increase and decrease buttons, emergency shut off button, and other buttons needed to control the stimulation therapy, as described above with regard to FIG. 3. The clinician and patient 12 may provide therapy efficacy feedback information, such as pain levels or medication taken, so that the therapeutic tree may be used to create an effective program path for the patient.

Processor 68 controls user interface 72, retrieves data from memory 70 and stores data within the memory. Processor 68 also controls the transmission of data through telemetry circuit 74 to stimulator 14. Memory 70 includes operation instructions for processor 68 and, in some embodiments, data related to the structure of the therapeutic tree and currently chosen program path. Memory 70 may also include a history of all tested or used program paths and efficacy input. Memory 70 may be a computer-readable medium comprising program instructions that cause processor 68 and programmer 20 to provide any of the functionality ascribed to them, and perform any of the methods described herein.

Telemetry circuit 74 allows the transfer of data to and from stimulator 14. Telemetry circuit 74 may communicate automatically with stimulator 14 at a scheduled time or when the telemetry circuit detects the proximity of the stimulator. Alternatively, telemetry circuit 74 may communicate with stimulator 14 when signaled by a user through user interface 72. Power source 76 may be a rechargeable battery, such as a lithium ion or nickel metal hydride battery. Other rechargeable or conventional batteries may also be used. In some cases, external programmer 20 may be used when coupled to an alternating current outlet.

In some embodiments, processor 68 may traverse a therapeutic tree based on efficacy feedback to identify stimulation parameters according to any of the techniques described herein. In some embodiments, efficacy feedback may take the form of patient or clinician feedback received via user interface 72. Additionally or alternatively, efficacy feedback may take the form of signals from one or more sensors 63, or information derived therefrom.

In some embodiments, processor 68 may receive such signals or information from stimulator 14. In other embodiments, processor 68 may receive the signals directly from sensors 63. For example, sensors 63 may be included within, or wired or wirelessly coupled to a programmer 20, 30.

Figure 6:
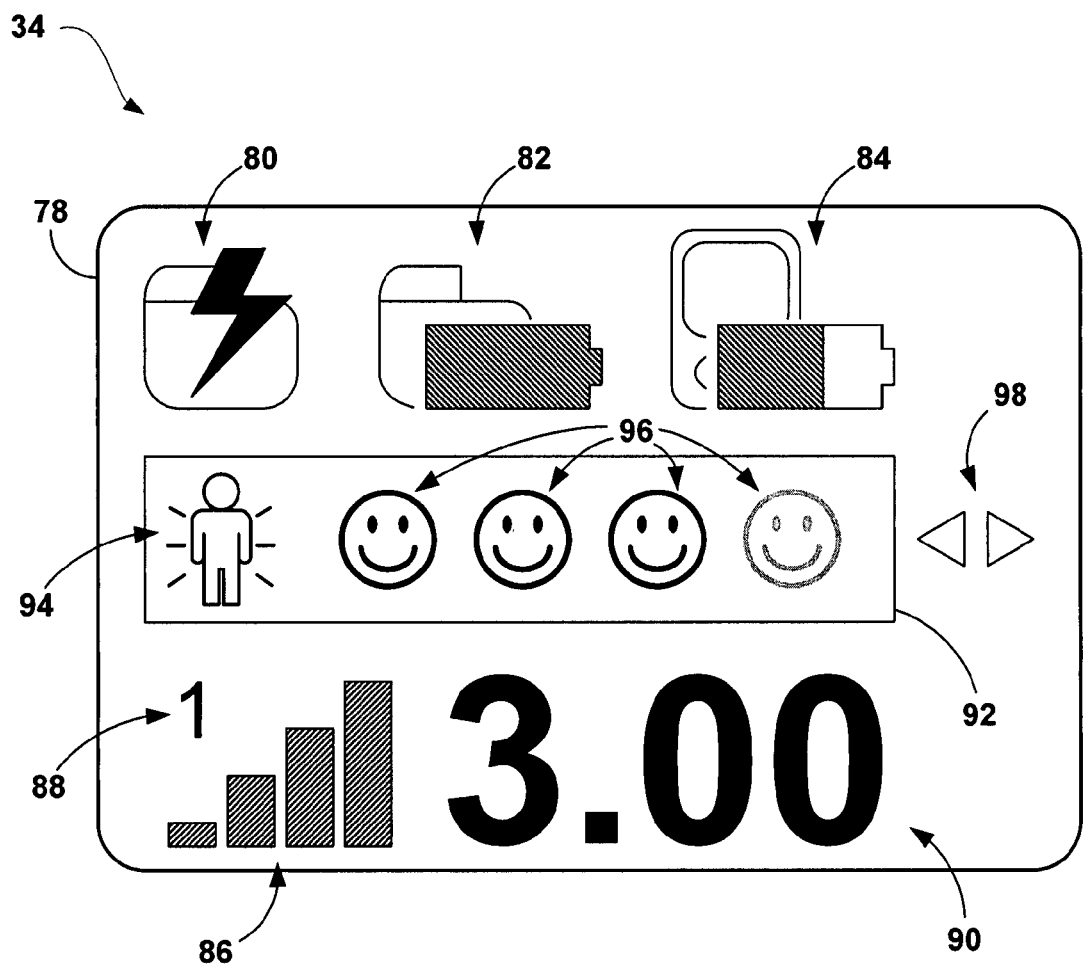
FIG. 6 is an example user interface for receiving patient input indicating therapy efficacy.

FIG. 6 is an example user interface for receiving patient or clinician input indicating therapy efficacy as perceived by the patient. In the example of FIG. 6, display 34 of programmer 20 provides user interface 78 to the user, such as patient 12. User interface 78 includes program number 88, parameter icon 86, information box 92, voltage amplitude 90, navigation arrows 98, stimulation icon 80, battery icon 82, and programmer battery 84. User interface 78 provides information to patient 12 regarding stimulation status and efficacy input from the patient. More or less information may be provided to patient 12, as desired by the clinician or patient.

Program number 88 and parameter icon 86 indicate the stimulation program currently used to provide stimulation therapy. In the example of FIG. 6, the program may be defined by the program path of a therapeutic tree. The therapeutic tree may also be used to change stimulation parameters of an existing program or create a new program from an existing program. Multiple programs may be created with the therapeutic tree and stored within programmer 20 and/or stimulator 14. In this manner, patient 12 may select from multiple stimulation programs for certain times of days, postures, activities, or other circumstances where a variation in stimulation may provide improved therapy.

Information box 92 contains information regarding the current stimulation program or programming effort. In the example of FIG. 6, information box 92 displays efficacy input from patient 12. Pain icon 94 indicates to the user that information box 92 is showing efficacy input that patient 12 has provided regarding the current stimulation therapy. Smile icons 96 indicate that the current stimulation therapy reduces pain in patient 12. As shown, three smile icons 96 indicates that patient 12 perceives little remaining pain during the therapy. The fourth smile icon 96 is grayed out because patient 12 has only indicated that the therapy is effective at eliminating most of the patient's pain. Fewer smile icons 96 may indicate that therapy is reducing pain but that some pain remains, while all four smile icons 96 indicates that the patient 12 cannot perceive any pain remaining. The number of smile icons 96 selected by patient 12 may indicate a percent efficacy of the therapy. For example, two smile icons 96 may indicate that the therapy is 50 percent effective. Generally, patient 12 or the clinician may continue creating new programs with the therapeutic tree until the program provides at least 50 percent efficacy, approximately equal to two smile icons 96.

Patient 12 may indicate one smile face 96 for every press of increase button 50 of programmer 20, for example. Conversely, frown icons may be shown to indicate that the therapy is not effective at reducing pain therapy. Further, multiple frown icons may indicate that stimulation therapy is increasing the pain of patient 12. In this case, programmer 20 may move within the therapeutic tree to attempt to find more efficacious stimulation parameters for reducing pain. In alternative examples, information box 92 may include numbers, letters, text, symbols, or any other indicator for the efficacy input provided by patient 12 or the clinician.

Voltage amplitude 90 displays the current voltage amplitude of the selected program 1 as shown by program number 88. Currently, the voltage amplitude is shown to be at 3.00 volts. If the voltage amplitude was at a maximum or minimum limit, a limit icon (not shown) may be displayed. In other embodiments, voltage amplitude 108 may display more or less decimal places to show amplitude precision as necessary for the stimulation therapy. Further, voltage amplitude 108 may be shown with graphs or text instead of numerals. In alternative embodiments where current amplitude, pulse rate, or pulse width may be adjusted, those parameter values may be displayed in place of voltage amplitude 108. In addition, patient 12 may make selections via user interface 78 to show the value of a desired one of a plurality of parameters and adjust it.

Stimulation icon 80 indicates the current status of stimulation therapy. Currently, the bolt is shown to indicate that stimulation is being delivered to patient 12 according to the active program group, i.e., program 1. In the case that stimulation is not being delivered, the bolt in icon 80 may not be shown. Stimulator battery 82 indicates the status of the battery in stimulator 14, which currently indicates that the battery is fully charged, or has a full charge in the case that the battery is not rechargeable. In other embodiments of stimulator battery 82, a percentage of battery life or battery life time remaining may be shown. Similar to stimulator battery 82, programmer battery 84 indicates the status of the battery in programmer 20. Currently, programmer battery 116 displays that the programmer battery has approximately two-thirds charge remaining. In alternative embodiments, other status indications may be used to show a percentage or time remaining of the programmer battery.

Arrows 98 provide a method for patient 12 to navigate to another screen or user interface of display 34. Patient 12 may highlight arrows 98, e.g., with a stylus or a button, and select it to move to another screen. In a similar manner, patient 12 may highlight other icons or areas of user interface 78 to make modifications to the associated aspects of the stimulation therapy. The components of user interface 78 are provided as an exemplary screen for a single program, while other layouts or arrangements of user interface 78 may be possible as well. User interface 78 may also show some elements in color if display 34 supports a color screen. In alternative embodiments, arrows 98 may not appear on user interface 78, and patient 12 may simply use control pad 28 to navigate between screens.

Figure 7:
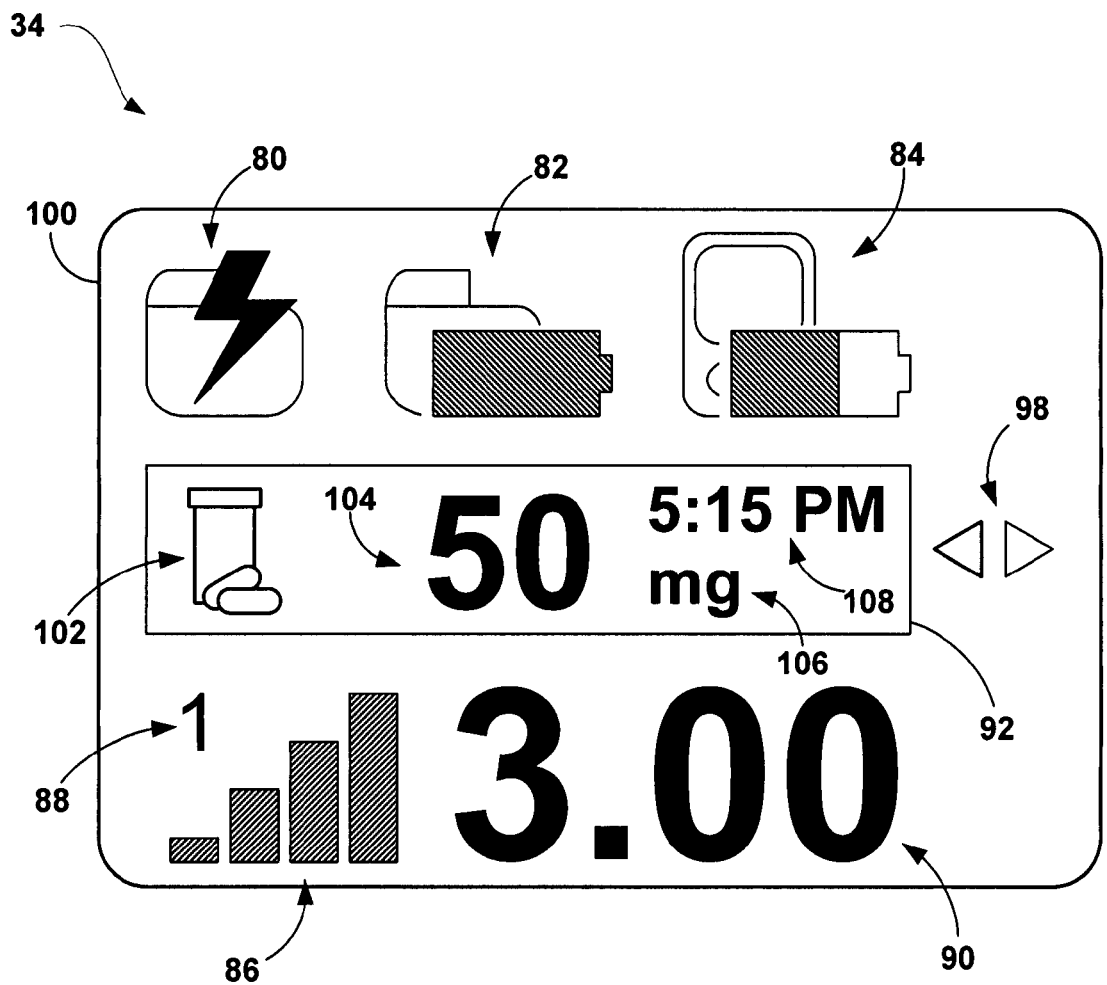
FIG. 7 is an example user interface for receiving medication dosage information from the patient.

FIG. 7 is an example user interface for receiving medication dosage information from the patient. In the example of FIG. 7, display 34 of programmer 20 provides user interface 100 to the user, such as patient 12. User interface 100 includes program number 88, parameter icon 86, information box 92, voltage amplitude 90, navigation arrows 98, stimulation icon 80, battery icon 84, and programmer battery 84, similar to user interface 78 of FIG. 6. User interface 100 provides information to patient 12 regarding stimulation status and medication taken by the patient. More or less information may be provided to patient 12, as desired by the clinician or patient.

Information box 92 contains information regarding the medication being taken by patient 12. In the example of FIG. 7, information box 92 displays the amount or dosage of medication currently taken as provided by patient 12. Medication icon 102 indicates to the user that information box 92 is ready to accept medication input and show the input to patient 12. Information box 92 is configured to accept medication input that corresponds to each instance patient 12 takes a dose of medication for treating pain. In order words, patient 12 must provide feedback to programmer 20 for each time during the day that medication is taken.

Dosage 104 indicates the volume or weight of medication just taken by patient 12. Units 106 indicates the units of dosage 104. As shown in FIG. 7, patient 12 has entered a medication input of 50 milligrams (mg). Patient 12 may use pad 28 to increase or decrease dosage 104 until the dosage matches the amount of drug taken by the patient. Patient 12 may also adjust units 106 to match the drug. For example, patient 12 may select grams (g) or milliliters (mL) depending on the dosage. In addition, timestamp 108 indicates to patient 12 the current time of day that programmer 20 will log with the medication input. In alternative examples, patient 12 may be able to adjust timestamp 108 to correctly indicate the exact time medication was taken by the patient. In some examples, the dosage of medication remains the same for patient 12. In this case, patient 12 may review information box 92 and enter the same information each time pain medication is taken.

Programmer 20 may associate the medication input with a single drug that patient 12 takes for pain management. In some examples, user interface 100 may allow patient 12 to select which type of drug was just taken when the patient takes multiple pain medications. Programmer 20 may estimate or determine the pain condition of patient 12 based upon the dosage and type of drug patient 12 has taken to help reduce perceived pain not managed by the stimulation therapy. Programmer 20 may include a lookup table or set of equations for determining the magnitude of patient pain based upon the strength and dosage of medication taken by patient 12. Programmer 20 may determine stimulation therapy efficacy, e.g., percent changes in efficacy, based on changes in the magnitude of patient pain as determined using such lookup tables or equations.

In alternative examples, patient 12 may not need to provide medication input every time that medication was taken. Patient 12 may create many medication inputs at the end of each day to approximate how much medication was taken. In this case, patient 12 may not be burdened by continuous logging of medication. Programmer 20 may provide daily, weekly, or monthly graphs of medication taken by patient 12 so that the patient can review trends in stimulation therapy efficacy. Patient 12 may use arrows 98 or pad 28 to scroll through recent medication inputs.

Figure 8:
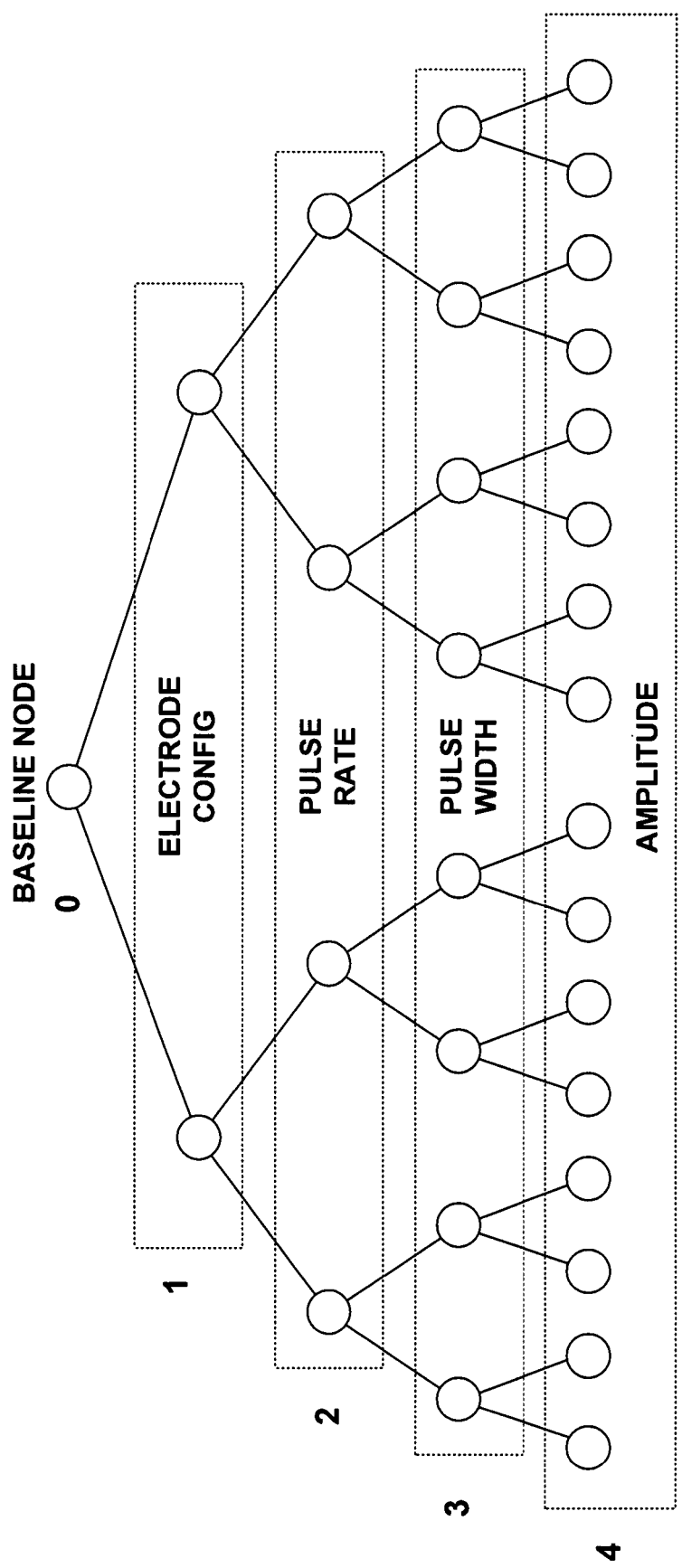
FIG. 8 is a diagram of a therapeutic tree structure for programming parameters associated with stimulation delivered by an implanted stimulator.

FIG. 8 is a diagram of a therapeutic tree structure for programming parameters associated with stimulation delivered by an implanted stimulator. As shown in FIG. 8, the therapeutic tree structure includes a baseline node, representing the baseline condition of the patient without stimulation therapy for treating pain, at a level 0 of the tree. At level 1, the tree includes two or more nodes specifying parameter sets for stimulation therapy. The parameter sets may specify electrode configurations (including combination and polarity, if applicable), pulse rate, pulse width and voltage or current amplitude. In some examples, stimulation parameters may include pulse charge density. A pulse change density may be a parameter that is similar to the combination of amplitude and pulse width, and may also consider the size of electrodes used to deliver pulses. The pulse charge density may be used in addition to or in place of the amplitude and/or pulse width parameters.

In the example of FIG. 8, the different nodes in level 1 represent identical values for pulse rate, pulse width and amplitude, but different electrode configurations. The pulse rate, pulse width and amplitude values are initial values that may be predetermined or selected by the clinician. Hence, the different nodes in level 1 represent different electrode configurations. As one example, one node may specify a combination of two electrodes as cathode and anode, while another node specifies the same combination of electrodes, but as anode and cathode. Hence, the level 1 nodes present different electrode configurations and/or polarities.

Each node in level 1 is connected to two or more nodes in level 2. Each node in level 2 has the same electrode configuration as the node to which it is connected above in level 1. In addition, the pulse width and amplitude values for the level 2 nodes may be the same as in level 1. However, in level 2, different nodes connected to the same level 1 node have different pulse rate values. Hence, level 2 represents different pulse rate adjustments to the stimulation program, given the other parameter values defined by the node above.

Each node in level 2 is connected to two or more nodes in level 3. Each node in level 3 has the same electrode configuration and pulse rate as the node to which it is connected above in level 2. In addition, the amplitude values for the level 3 nodes may be the same in level 1. In level 3, however, different nodes connected to the same level 2 node have different pulse width values. Hence, level 3 represents different pulse width adjustments to the stimulation program, given the other parameter values defined by the node above.

Each node in level 3 is connected to two or more nodes in level 4. Each node in level 4 has the same electrode configuration, pulse rate and pulse width as the node to which it is connected above in level 3. However, different nodes connected to the same level 3 node have different amplitude values. Hence, level 4 represents different amplitude adjustments to the stimulation program, given the other parameter values defined by the node above.

The physician, patient, programmer and/or stimulator travel along a path through the therapeutic tree based on efficacy information provided by efficacy feedback from the patient and/or clinician, or sensors 63. For example, the clinician or patient may control the path through the tree by entering efficacy information into programmer 20, in which case the programmer may select the next node in the tree, either automatically or the clinician or patient confirms the selection.

In addition, in some embodiments, programmer 20 or stimulator 14 may define the program path automatically based on efficacy input received from the patient or clinician via the programmer, or efficacy feedback received from one or more sensors 63. In each case, relative efficacy provided by stimulation parameters associated with the nodes serves to guide the program along the tree to the next node.

In the example of FIG. 8, the order of levels proceeds from electrode combination/polarity at level 1, to pulse rate at level 2, pulse width at level 3, and amplitude at level 4. Hence, the therapy parameters are prioritized such that electrode combination/polarity is used for high-level coarse tuning, as it is perceived as heavily impacting stimulation efficacy, e.g., due to it role in positioning the stimulation relative to a target tissue site.

The other parameters are prioritized in order of impact to provide progressively finer tuning of the stimulation parameter set. For example, after electrode combination/polarity, pulse rate may be viewed as having the next largest impact on efficacy, followed by pulse width and pulse amplitude. The prioritization shown in FIG. 8 is for purposes of example, however, and should not be considered limiting of the invention. Rather, in other embodiments or implementations, the order of parameters among the hierarchy of the therapeutic tree may be subject to variation.

Although each level in the example tree of FIG. 8 represents bifurcated branching from a node above, i.e., from one node to two nodes, each node may branch to two, three, or more nodes in the next level below. In addition, although FIG. 8 shows four levels, not counting the baseline node, additional levels may be added to the tree for additional stimulation parameters or to permit more fine tuning of any of the parameters adjusted in the levels above. Accordingly, the tree in FIG. 8 is provided for purposes of illustration, and may be simpler or more complex for a given stimulation pain therapy implementation.

Furthermore, the tree structure may be created or modified based on user input or other considerations, which may be specific to a patient, therapy, or stimulator or lead configuration. For example, the range of parameter values in each level may be configured based on the limitations of a system 10, or based on patient comfort and safety considerations. Available stimulation amplitudes, for example, may be limited based on considerations such as size of electrodes and charge density.

The therapeutic tree may also be used to create new programs from existing programs. In this manner, programs created with the therapeutic tree may be grouped together according to their use, such as the time of day, posture, activity, or other circumstance where a variation in stimulation between the grouped programs may provide improved therapy for patient 12. For example, any new program created from an existing program with the therapeutic tree may be grouped with the existing program. Alternatively, a new program may be added to a current group by using the therapeutic tree; however, the therapeutic tree may eliminate any parameters that have been found to be ineffective with other programs associated with that specific group of programs.

Figure 9:
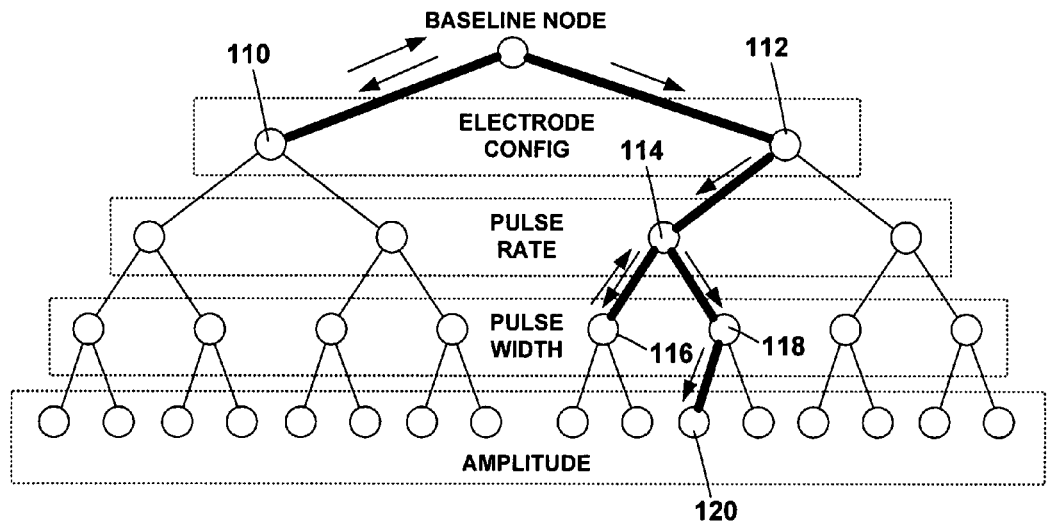
FIG. 9 is a diagram illustrating traversal of the therapeutic tree to define an example program path.

FIG. 9 is a diagram illustrating traversal of the therapeutic tree to define an example program path. As shown in FIG. 9, the program path first traverses from the baseline node downward to a first node 110 in level 1, which defines a particular electrode combination and/or polarity. In this example, the efficacy improvement produced by node 110 relative to the patient's baseline condition, i.e., without therapy, is less than a specified threshold level, e.g., 50%. Accordingly, the program path progresses no further down the path connected to node 110, and instead reverses through the baseline node to the second node 112 at level 1. In this case, node 112 presents an efficacy improvement in excess of 50%, and the program path proceeds to the next node 114, which resides in level 2 and specifies a change in pulse rate, while maintaining the electrode configuration and other parameters of node 112.

The threshold level that patient 12 uses to determine the efficacy of a program may depend upon the baseline pain or disorder perceived by the patient compared to a completely treated condition. A therapy that reaches a 50 percent efficacy threshold may successfully make patient 12 feel like half of the pain or disorder is gone while half of the pain or disorder is still perceived. For example, patient 12 may use a disorder or pain scale that ranges from 1 to 10, where 10 indicates that the pain or disorder is unbearable and 1 indicates a disorder free, pain free, or normal condition. Patient 12 may indicate that their untreated baseline condition is a 8. For the program to provide 50 percent efficacy, patient 12 would need to indicate a condition of 4 on the 1 to 10 scale. Alternatively, patient 12 may indicate two smile icons 96 out of four smile icons in user interface 78 of FIG. 6. In other examples, the 50 percent threshold may apply to 50 percent fewer sleep interruptions during the night or being able to stand for 50 percent greater amount of time. The thresholds may be different according to the type of stimulation therapy, patient condition, or patient desires.

Node 114 defines stimulation parameters that are found to yield an efficacy improvement in excess of 50%. As a result, the program path continues along a path connected to node 114. In particular, the program path first evaluates parameters associated with node 116 in level 3. Node 116 represents an adjustment to pulse width, while maintaining the electrode configuration and pulse rate specified by node 114. However, the efficacy feedback reveals that node 116 does not achieve an efficacy improvement of greater than 50%. For this reason, the program path returns to node 114 and traverses another branch of node 114 to node 118.

At node 118, the stimulation parameters produce an efficacy improvement in excess of 50% relative to the baseline condition of the patient. In response, the program path proceeds to node 120 in level 4, which represents a change in amplitude but otherwise maintains the parameter values associated with node 118 in level 3. Generally, a 50 percent efficacy improvement relative the baseline patient condition is required to continue along a path extending from a particular node. However, once a program path reaches the bottom of the tree, e.g., level 4, additional program paths may still be created until a higher percent efficacy is reached, e.g., 80%.

Once patient 12 is experiencing an 80% efficacy improvement relative to the baseline condition along a given program path, the process may be terminated at the current node in that program path or the process may only proceed to fine tune parameters using lower levels along the same path. As mentioned previously, the 50% and 80% efficacy thresholds are only examples, and the clinician may utilize thresholds that are any percentage. Further, representations or measures of efficacy or efficacy improvement other than percentages may be used in some embodiments.

Figure 10:
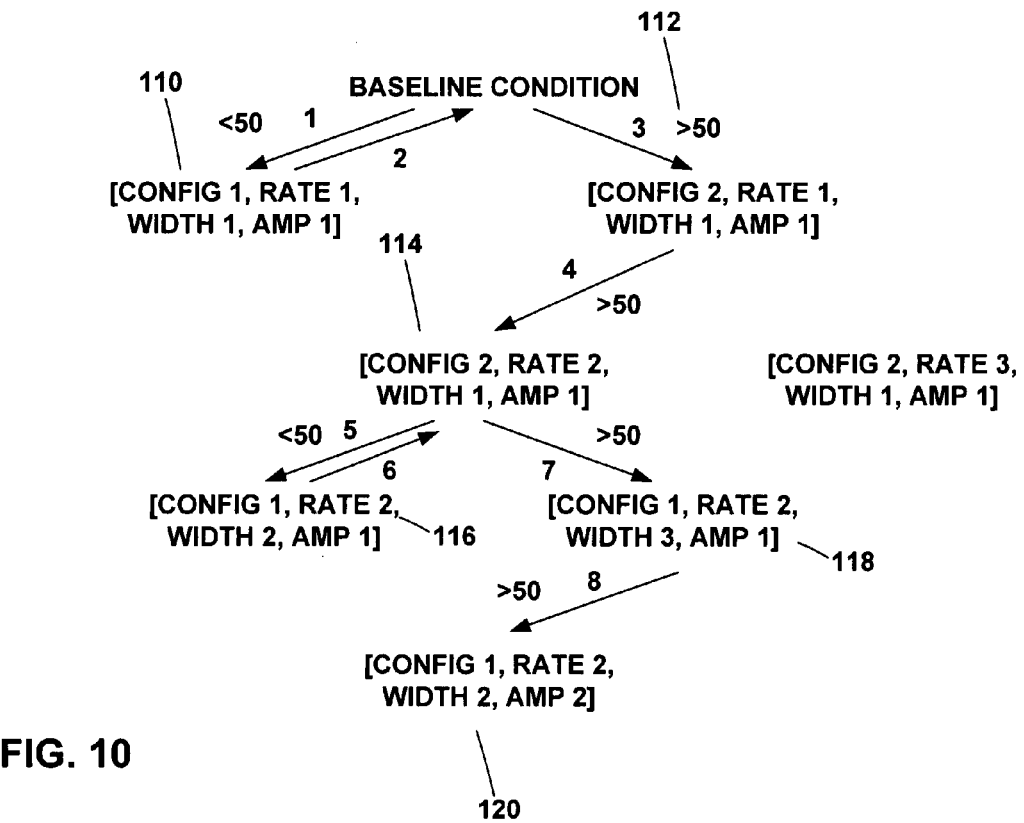
FIG. 10 is a diagram illustrating the program path of FIG. 9 in terms of parameter sets associated with nodes in the program path.

FIG. 10 is a diagram illustrating the program path of FIG. 9 in terms of parameter sets associated with nodes in the program path for stimulation pain therapy. In particular, FIG. 10 shows parameter sets corresponding to nodes 110, 112, 114, 116, 118 and 120 of FIG. 9. In addition, FIG. 10 numbers the steps along the program path as steps 1, 2, 3, 4, 5, 6, 7, and 8. As shown, nodes 110 and 112 include similar parameter sets but different electrode configurations. In particular, node 110 specifies [Config 1, Rate 1, Width 1, Amp 1] and node 112 specifies [Config 2, Rate 1, Width 1, Amp 1], where configuration represents electrode combination/polarity, rate represents pulse rate, width presents pulse width and amp represents amplitude. In the next level, FIG. 10 shows node 114 in terms of the parameter set [Config 2, Rate 2, Width 1, Amp 1]. In this case, the electrode configuration, pulse width and amplitude are the same as node 112 above, but Rate 2 is different from Rate 1, representing a pulse rate adjustment.

Figure 11:
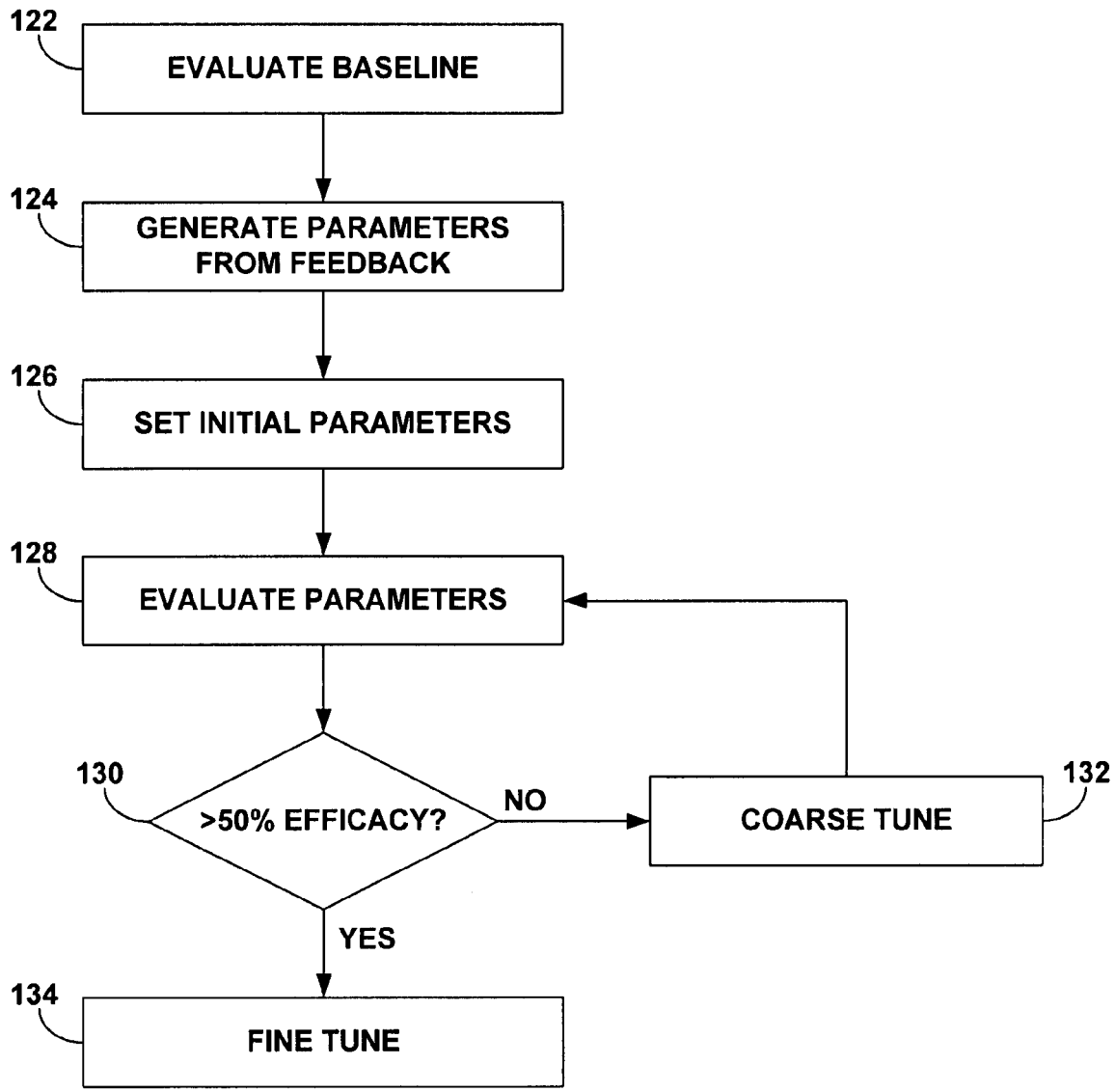
FIG. 11 is a flow chart illustrating a technique for programming the implanted stimulator.

FIG. 11 is a flow chart illustrating an example technique for programming the implanted stimulator. Although described with reference to programmer 20, the example technique may be performed by other components of systems 10, 22, such as stimulator 14.

As shown in FIG. 11, the clinician aids patient 12 in initially finding a program path to deliver stimulation therapy. First, a baseline condition, e.g., the initial condition of the patient without stimulation, is evaluated (122). Evaluating the initial condition may include providing feedback to criteria from external programmer 20 describing the severity of chronic pain perceived by the patient before stimulation is applied. Evaluating the initial condition may additionally or alternatively evaluating signals from one or more physiological parameter sensors, or metrics derived from such signals.

From the baseline information, external programmer 20 generates initial parameters to begin stimulation therapy (124). The initial parameters may be specified or approved by the clinician. At this point in the process, the therapeutic tree has not yet been used. The clinician uses external programmer 20 to begin initial stimulation (126) to evaluate nodes in the therapeutic tree.

The stimulation therapy from the initial parameters is evaluated (128). In some cases, the therapy may have to be evaluates over a long period of time, such as 24 hours or more. If the feedback from patient 12 or sensors 63 indicates that the initial stimulation therapy is approximately greater than a 50% improvement (130) relative to the baseline condition, external programmer 20 moves directly into fine tuning, i.e., by moving to a lower level of the therapeutic tree (134). If the therapy is less than 50 percent effective (144), external programmer 20 moves to gross or coarse tune by moving to another node of the first level of the therapeutic tree to more coarsely change the stimulation therapy (132). Then, patient 12 evaluates the new parameters of the gross tune (128). Fine tuning further follows the therapeutic tree and is described in FIG. 12.

Feedback from patient 12 or the clinician may be in the form of efficacy input related to the ability of the stimulation to reduce pain, medication input, or both. Initially, the program path of the therapeutic tree may be created through efficacy input. Efficacy input may additionally or alternatively include sensor-based feedback reflecting how much the pain has been reduced through stimulation.

Figure 12:
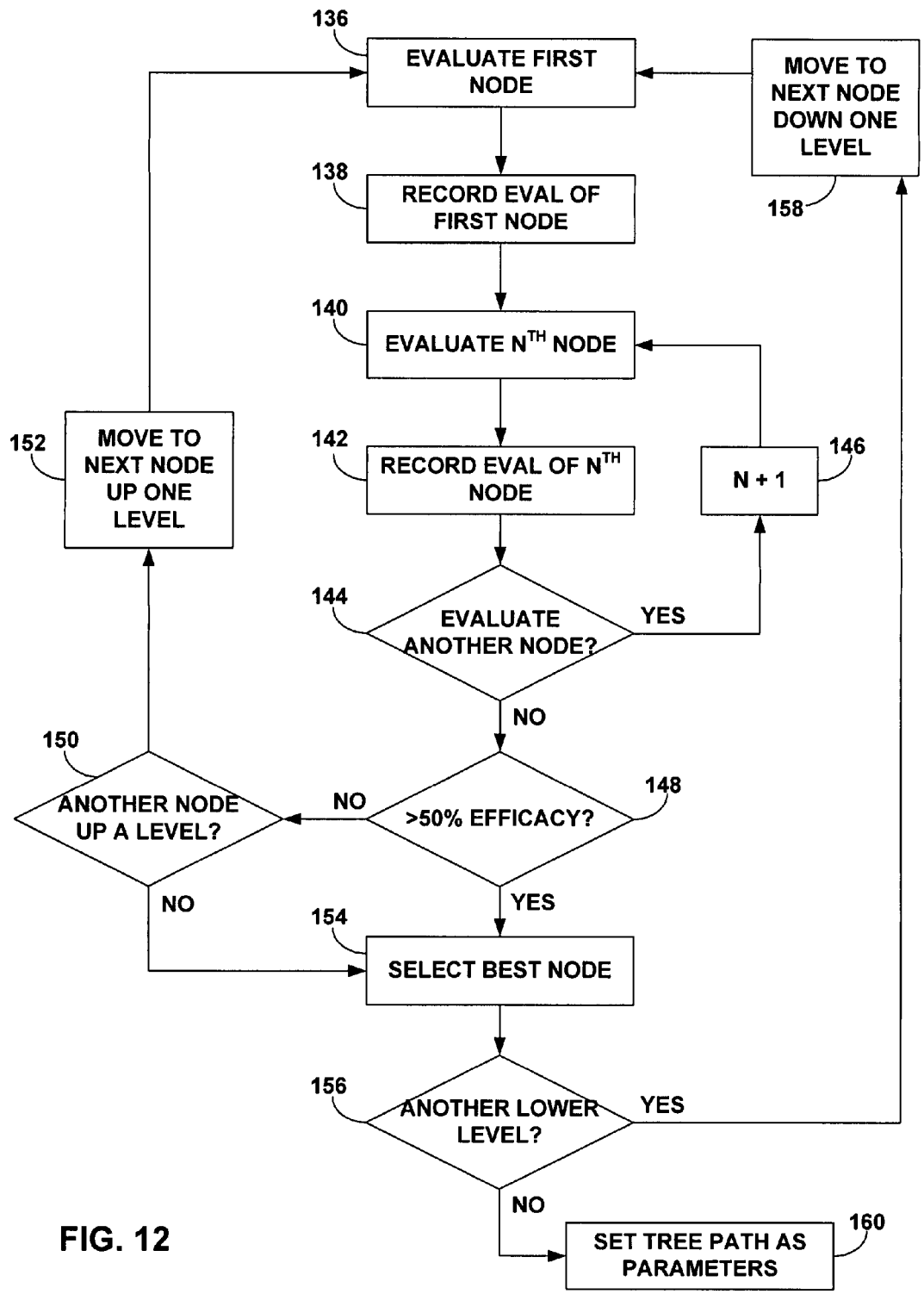
FIG. 12 is a flow chart illustrating a technique for fine tuning the programming of the implanted stimulator.

FIG. 12 is a flow chart illustrating a technique for fine tuning the programming of the implanted stimulator 14. Although described with reference to programmer 20, the example technique may be performed by other components of systems 10, 22, such as stimulator 14. Furthermore, although described in the context of patient input as efficacy feedback, the technique may additionally or alternatively be practiced with sensor signals, or values derived therefrom, as the efficacy feedback.

As shown in FIG. 12, the therapeutic tree is used to fine tune stimulation therapy by creating a program path to best treat the pain of patient 12. The patient first evaluates the first node of the second level (136). Patient 12 records the evaluation of the first node using programmer 20 (138). Next, patient 12 evaluates the Nth node (140) and the patient records the evaluation of the Nth node (142). If there is another node of the second level to evaluate (144), programmer 20 adds 1 to the Nth node (146) and patient 12 evaluates the N+1 node (140). If there is no other node to evaluate, programmer 20 determines if any of the evaluated nodes reached greater than 50 percent efficacy (148).

If no nodes of the second level provide greater than 50 percent efficacy, external programmer 20 checks if there is a level up one level from the current position on the therapeutic tree (150). If there is another level, programmer 20 moves up one level (152) and patient 12 evaluates another node of that upper level (136). If there is no level higher up the tree (150) or one of the evaluated nodes is greater than 50 percent efficacious (138), external programmer 20 selects the best node (154).

If there is a lower lever on the therapeutic tree (156), programmer 20 moves to the lower level, i.e. the third level in this example (158), and another node of the third level is evaluated (136). If there are no lower levels on the therapeutic tree to evaluate (156), programmer 20 sets the current program path as the nodes, or stimulation parameters, to deliver stimulation therapy to patient 12.

In alternative examples, programmer 20 may select the best node evaluated and move down a level if no nodes provided an efficacy greater than 50 percent. It may be possible that parameters of lower levels can create a program that elicits a better than 50 percent efficacy. In other examples, such as trial stimulation, programmer 20 may quit evaluation with the therapeutic tree once therapy efficacy reaches 50 percent to save programming time. As mentioned previously, alternative efficacy thresholds may be selected by patient 12 or the clinician.

Also, further fine tuning steps may be performed after reaching an efficacy threshold or a lowest level in the tree. For example, a stimulator or programmer may be programmed, based on knowledge of nerve activation curves, to further fine tune a desirable programming path by adjusting amplitude and pulse width in concert to continue activating the same nerves. Although activating the same nerves, such adjustments may result in improved comfort, e.g., reduced side effects such as numbness, tingling, jolting with movement, or nausea.

Similar to FIG. 11, feedback from patient 12 or the clinician may be in the form of efficacy input related to the ability of the stimulation to reduce pain, medication input, or both. Initially, the program path of the therapeutic tree may be created through efficacy input. Efficacy input may include how much the pain has been reduced in one or more postures or activities or which activities are enabled by reducing pain through stimulation. However, programmer 20 may be capable of incorporating medication input in order to create the best program path according to all feedback related to the condition of patient 12.

Figure 13:
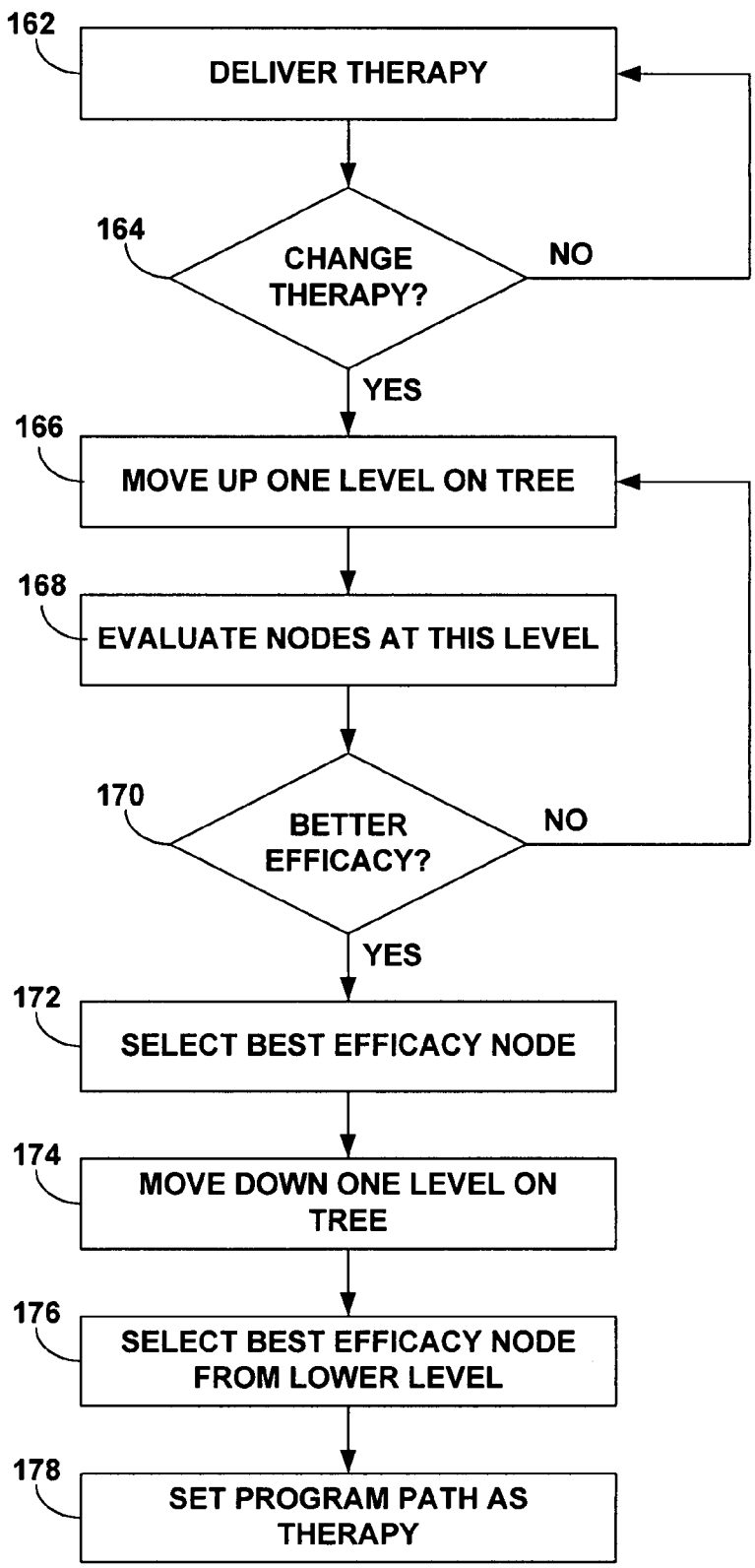
FIG. 13 is a flow chart illustrating a technique for fine tuning stimulation therapy during therapy delivery.
Figure 14:
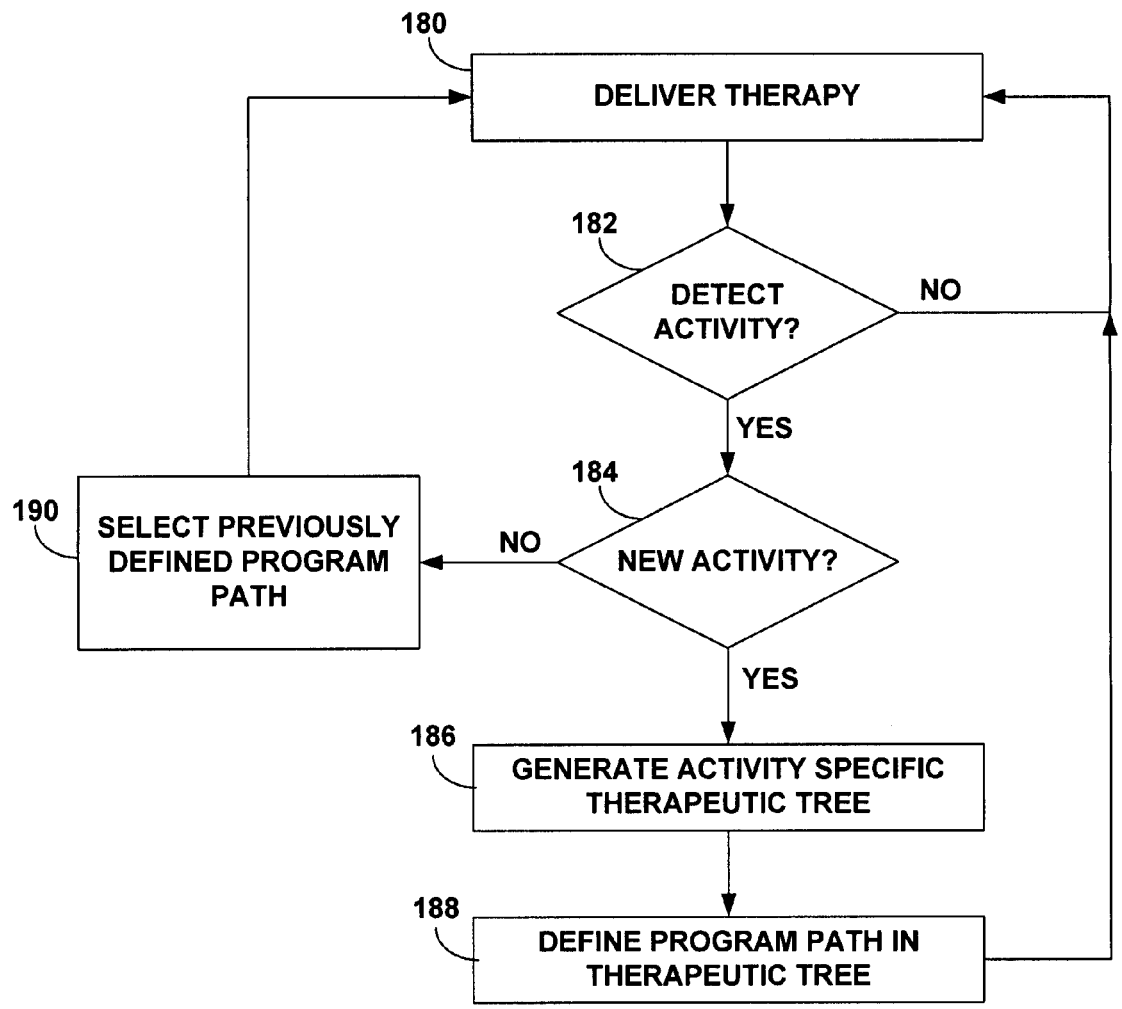
FIG. 14 is a flow chart illustrating a technique for identifying and subsequently using, for delivery of stimulation therapy, an activity-specific path in a therapeutic tree.

FIG. 13 is a flow chart illustrating a technique for fine tuning stimulation therapy during chronic therapy delivery. Although described with reference to programmer 20, the example technique may be performed by other components of systems 10, 22, such as stimulator 14. Furthermore, although described in the context of patient input as efficacy feedback, the technique may additionally or alternatively be practiced with sensor signals, or values derived therefrom, as the efficacy feedback.

As shown in FIG. 13, the program path that defines stimulation therapy may be modified during therapy. Stimulator 14 delivers therapy to patient 12 (162), and if there is no indication to change therapy (164), therapy continues unchanged. The indication to change therapy may be from stimulator 14, patient 12, or the clinician. The indication may be direct parameter change input from patient 12, a change in efficacy input, or a change in sensor or medication based feedback. The amount of change that triggers the use of the therapeutic tree may be predefined or selected by patient 12 or the clinician. For example, therapy efficacy may need to drop by 10 percent or more to change the program by using the therapeutic tree. If therapy should change (164), programmer 20 moves up one level on the therapeutic tree (166). Patient 12 evaluates the nodes at this level (168) such that programmer 20 may determine if any nodes provide better efficacy (170). If no nodes provide better efficacy, programmer 20 moves up one more level on the therapeutic tree (166).

If at least one evaluated node provides better efficacy (170), programmer 20 selects the best efficacy node based upon patient 12 feedback (172). Programmer 20 moves down one level on the therapeutic tree from the selected node (174) and programmer 20 selects the best efficacy based upon the additional patient 12 feedback (176). Programmer 20 sets the program path as the stimulation parameters for therapy and delivers the stimulation to patient 12 (178).

Similar to FIG. 11, feedback from patient 12 or the clinician may be in the form of efficacy input related to the ability of the stimulation to reduce pain, medication input, or both. Initially, the program path of the therapeutic tree may be created through efficacy input. Efficacy input may include who much the pain has been reduced in one or more postures or activities or which activities are enabled by reducing pain through stimulation. However, programmer 20 may be capable of incorporating medication input in order to create the best program path according to all feedback related to the condition of patient 12.

Furthermore, medication input may be used to indicate how often to revisit the therapeutic tree structure for reprogramming. For example, to the extent that the patient is given some control of dosage amount or frequency, increases in these values may indicate a need to reprogram stimulation therapy for improved efficacy. Additionally, the extent of use or medication may color the any subjective evaluation of efficacy. For example, subjective efficacy indications may be weighted based on whether the patient's condition was also being alleviated by a drug therapy at the same time. Also, patient input on medication use may impact the time between evaluations of new branches on the tree. For example, a programmer or stimulator may wait until a medication dose is effective, or has run its course, to try a new programming path in the tree structure.

FIG. 18 is a flow chart illustrating a technique for identifying and using an activity-specific path through a therapeutic tree. As shown in FIG. 18, the clinician may deliver therapy to patient 12 via a program path of a therapeutic tree, e.g., a tree structure, as described above (180). However, patient 12 may benefit from a change in the stimulation therapy according to the specific activity of the patient. Therefore, a programmer or stimulator may check to see whether a particular activity undertaken by a patient has been detected (182). Example activities include, sleeping, running, golfing, swimming, speaking, or particular work or leisure related activities. The activity may be detected based on an input from a user, e.g., the clinician or patient 12, or a signal from any one or more of the sensors discussed above. For example, sleep may be detected using any of the sensors and techniques described herein, and particular physical activities may be detected based on comparison of signals from one or more accelerometers, piezoelectric elements, and/or EMG electrodes, as examples, to various thresholds or templates.

If the programmer or stimulator does not detect an activity, therapy continues as presently programmed (180). If the programmer or stimulator does detect an activity, the programmer or stimulator determines whether the activity is a new activity (184), e.g., one for which an activity-specific program path has not already been determined. If the activity is new, the programmer or stimulator may generate a therapeutic tree specific for the activity (186). For example, if the activity change indicates that patient 12 is sleeping, the activity specific therapeutic tree may be structured or weighed according to the needs of the activity. Parameters may become more or less important to therapy efficacy, or some parameter values, e.g., electrode combinations, may not be provided in the tree. Further, the thresholds used for traversing the tree may be specific to the activity. Such tree-to-tree variations may be user-configurable.

The programmer or stimulator may then define a program path through the therapeutic tree based on performance feedback received during delivery of stimulation when the patient is engaged in the detected activity (188). The defined path, e.g., the therapy parameters defined by the path, may be associated with the activity, and therapy may be delivered according to the newly defined path (180). If the activity is subsequently detected (182, 184), the stimulator or programmer may select the previously defined program path associated with the activity (190) for delivery of therapy (180).

In some embodiments, initial detecting of the activity may be based on user input. The programmer or stimulator may monitor sensor signals after receiving the user input to develop a template for subsequently detecting the activity. In other embodiments, both initial and subsequent detection of the activity may be by user input or by sensor.

The activity specific tree structure may be specific to any activity of patient 12. Example activities may include sleeping, sitting, standing, walking, running, talking, playing a sport, driving, or any other event or activity that patient 12 may participate in during the day. In some examples, programmer 20 may have activity specific tree structures preprogrammed for patient 12. In other examples, the clinician or patient 12 may need to create each activity specific tree structure as needed for therapy.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure.

Many embodiments of the invention have been described. Various modifications may be made without departing from the scope of the claims. For example, although the invention has been generally described in conjunction with implantable stimulation devices, external stimulators, trial stimulators, drug delivery devices, or any other therapy device may be programmed through the use of a therapeutic tree and other methods described herein to treat pain disorders and conditions. These and other embodiments are within the scope of the following claims.

The invention claimed is:

1. A method for providing electrical stimulation therapy to treat pain, the method comprising:
   defining a tree structure having a plurality of levels and a plurality of nodes in each of the levels, wherein each of the nodes is interconnected with at least one node above and at least two nodes below in the tree structure, each node defines respective values for a set of electrical stimulation parameters, the nodes in each level specify an adjustment to a value of at least one type of stimulation parameter, the nodes in different levels specify adjustments to the value of different types of stimulation parameters, and the adjustments to the value of each type of stimulation parameter are limited to a single level of the tree structure;
   defining a program path through the tree structure along a series of the interconnected nodes for which efficacy of stimulation therapy delivered according to the stimulation parameters defined by the nodes in treating pain exceeds a threshold level;
   selecting one of the nodes in the program path; and
   delivering the stimulation therapy to a patient based on the parameters defined by the selected node to treat patient pain.

2. The method of claim 1, wherein the stimulation therapy comprises at least one of spinal cord stimulation, deep brain stimulation, peripheral nerve stimulation, and peripheral nerve field stimulation.

3. The method of claim 1, further comprising specifying which stimulation parameters are adjusted at which levels of the tree based on user input.

4. The method of claim 1, further comprising receiving efficacy input indicating the efficacy of the delivered stimulation.

5. The methods of claim 4, wherein receiving efficacy input comprises:
   prompting a user to provide the efficacy input;
   receiving the efficacy input via an external programmer; and
   displaying the efficacy input to the user.

6. The method of claim 4, wherein receiving efficacy input comprises receiving the efficacy input via at least one sensor that measures a physiological parameter.

7. The method of claim 1, further comprising receiving medication input from a user indicating a dosage of medication taken by the patient.

8. The method of claim 1, wherein the tree structure comprises at least four levels.

9. The method of claim 8, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

10. The method of claim 1, wherein the stimulation parameters include stimulation electrode configuration, stimulation pulse rate, stimulation pulse width, and stimulation pulse amplitude.

11. The method of claim 1, further comprising defining the tree structure within an external programmer associated with an implantable electrical stimulator.

12. The method of claim 1, further comprising:
   detecting an activity undertaken by the patient;
   defining a program path specific to the activity through the tree structure along a series of the interconnected nodes for which performance feedback regarding stimulation therapy delivered according to the stimulation parameters defined by the nodes during the activity exceeds a threshold level;
   subsequently detecting the activity; and
   delivering the stimulation therapy to the patient according to the previously defined program path specific to the activity.

13. A system for providing electrical stimulation pain therapy, the system comprising:
   a memory defining a tree structure having a plurality of levels and a plurality of nodes in each of the levels, wherein each of the nodes is interconnected with at least one node above and at least two nodes below in the tree structure, each node defines respective values for a set of electrical stimulation parameters, the nodes in each level specify an adjustment to a value of at least one type of stimulation parameter, the nodes in different levels specify adjustments to the value of different types of stimulation parameters, and the adjustments to the value of each type of stimulation parameter are limited to a single level of the tree structure; and
   a processor that is configured to define a program path through the tree structure along a series of the interconnected nodes for which efficacy of stimulation pain therapy delivered according to the stimulation parameters defined by the nodes exceeds a threshold level, selects one of the nodes in the program path, and controls delivery of the stimulation pain therapy to a patient based on the parameters defined by the selected node to treat patient pain.

14. The system of claim 13, wherein the stimulation therapy comprises at least one of spinal cord stimulation, deep brain stimulation, peripheral nerve stimulation, and peripheral nerve field stimulation.

15. The system of claim 13, wherein the processor specifies which stimulation parameters are adjusted at which levels of the tree based on user input.

16. The system of claim 13, wherein the processor receives efficacy input indicating the efficacy of the delivered stimulation pain therapy.

17. The system of claim 16, further comprising a user interface, wherein:
the processor prompts the user via the user interface to provide the efficacy input;
the processor receives the efficacy input from a user via the user interface; and
the user interface displays the efficacy input to the user.

18. The system of claim 16, further comprising a sensor that measures a physiological parameter of the patient, wherein the processor receives the efficacy input from the sensor.

19. The system of claim 13, wherein the processor receives a medication input from a user indicating a dosage of medication taken by the patient.

20. The system of claim 13, wherein the tree structure comprises at least four levels.

21. The system of claim 20, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

22. The system of claim 13, wherein the stimulation parameters include stimulation electrode configuration, stimulation pulse rate, stimulation pulse width, and stimulation pulse amplitude.

23. The system of claim 13, wherein the processor resides within an external programmer associated with an implantable electrical stimulator.

24. The system of claim 13, wherein the processor:
detects an activity undertaken by the patient;
defines a program path specific to the activity through the tree structure along a series of the interconnected nodes for which performance feedback regarding stimulation therapy delivered according to the stimulation parameters defined by the nodes during the activity exceeds a threshold level;
subsequently detects the activity; and
controls delivery of the stimulation therapy to the patient according to the previously defined program path specific to the activity.

25. A non-transitory computer-readable medium comprising instructions to cause a processor to:
define a tree structure having a plurality of levels and a plurality of nodes in each of the levels, wherein each of the nodes is interconnected with at least one node above and at least two nodes below in the tree structure, each node defines respective values for a set of electrical stimulation parameters, the nodes in each level specify an adjustment to a value of at least one type of stimulation parameter, the nodes in different levels specify adjustments to the value of different types of stimulation parameters, and the adjustments to the value of each type of stimulation parameter are limited to a single level of the tree structure;
define a program path through the tree structure along a series of the interconnected nodes for which efficacy of stimulation pain therapy delivered according to the stimulation parameters defined by the nodes exceeds a threshold level;
select one of the nodes in the program path; and
control delivery of the stimulation pain therapy to a patient based on the parameters defined by the selected node to treat patient pain.

26. The computer-readable medium of claim 25, wherein the stimulation therapy comprises at least one of spinal cord stimulation, deep brain stimulation, peripheral nerve stimulation, and peripheral nerve field stimulation.

27. The computer-readable medium of claim 25, wherein the instructions cause the processor to specify which stimulation parameters are adjusted at which levels of the tree based on user input.

28. The computer-readable medium of claim 25, wherein the instructions cause the processor to receive efficacy input indicating the efficacy of the delivered stimulation pain therapy.

29. The computer-readable medium of claim 28, wherein the instructions that cause the processor to receive the efficacy input comprise instructions that cause the processor to:
prompt the user to provide the efficacy input;
receive the efficacy input via an external programmer; and
display the efficacy input to the user.

30. The computer-readable medium of claim 28, wherein the instructions tat cause the processor to receive the efficacy input further comprise instructions that cause the processor to receive the efficacy input from a sensor that measures a physiological parameter of the patient.

31. The computer-readable medium of claim 25, further comprising instructions that cause the processor to receive medication input from a user indicating a dosage of medication taken by the patient.

32. The computer-readable medium of claim 25, wherein the tree structure comprises at least four levels.

33. The computer-readable medium of claim 32, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

34. The computer-readable medium of claim 25, wherein the stimulation parameters include stimulation electrode configuration, stimulation pulse rate, stimulation pulse width, and stimulation pulse amplitude.

35. The computer-readable medium of claim 25, wherein the instructions cause the processor to define the tree within an external programmer associated with an implantable electrical stimulator.

36. The computer-readable medium of claim 25, further comprising instructions that cause the processor to:
detect an activity undertaken by the patient;
define a program path specific to the activity through the tree structure along a series of the interconnected nodes for which performance feedback regarding stimulation therapy delivered according to the stimulation parameters defined by the nodes during the activity exceeds a threshold level;
subsequently detect the activity; and
control delivery of the stimulation therapy to the patient according to the previously defined program path specific to the activity.

* * * * *

UNITED STATES PATENT AND TRADEMARK OFFICE
CERTIFICATE OF CORRECTION

PATENT NO. : 7,801,619 B2  Page 1 of 1
APPLICATION NO. : 11/799114
DATED : September 21, 2010
INVENTOR(S) : Martin T. Gerber et al.

It is certified that error appears in the above-identified patent and that said Letters Patent is hereby corrected as shown below:

Column 30
Lines 12-13, "of the delivered stimulation." should read -- of the delivered stimulation therapy. --

Signed and Sealed this
Twenty-second Day of March, 2011

David J. Kappos
*Director of the United States Patent and Trademark Office*